(12) United States Patent
Sanchez

(10) Patent No.: US 11,537,917 B1
(45) Date of Patent: Dec. 27, 2022

(54) SMART RING SYSTEM FOR MEASURING DRIVER IMPAIRMENT LEVELS AND USING MACHINE LEARNING TECHNIQUES TO PREDICT HIGH RISK DRIVING BEHAVIOR

(71) Applicant: BlueOwl, LLC, San Francisco, CA (US)

(72) Inventor: Kenneth Jason Sanchez, San Francisco, CA (US)

(73) Assignee: BlueOwl, LLC, San Francisco, CA (US)

( * ) Notice: Subject to any disclaimer, the term of this patent is extended or adjusted under 35 U.S.C. 154(b) by 154 days.

(21) Appl. No.: 16/913,446

(22) Filed: Jun. 26, 2020

Related U.S. Application Data

(60) Provisional application No. 62/877,391, filed on Jul. 23, 2019.

(51) Int. Cl.
*B60W 40/08* (2012.01)
*G06N 5/04* (2006.01)
(Continued)

(52) U.S. Cl.
CPC .............. *G06N 5/04* (2013.01); *B60W 40/08* (2013.01); *B60W 50/14* (2013.01); *G06N 20/00* (2019.01);
(Continued)

(58) Field of Classification Search
CPC ......... G06N 5/04; G06N 20/00; B60W 40/08; B60W 50/14; B60W 2040/0836;
(Continued)

(56) References Cited

U.S. PATENT DOCUMENTS

| 6,097,480 A | 8/2000 | Kaplan |
| 6,560,993 B1 | 5/2003 | Bosque et al. |

(Continued)

FOREIGN PATENT DOCUMENTS

| CN | 104799509 A | 7/2015 |
| CN | 106360895 A | 2/2017 |

(Continued)

OTHER PUBLICATIONS

Adafruit, p. 1-2, available at: https://www.adafruit.com/product/2806, published Jun. 2019 (Year: 2019).*

(Continued)

*Primary Examiner* — Kenneth J Malkowski
(74) *Attorney, Agent, or Firm* — Faegre Drinker Biddle & Reath LLP

(57) ABSTRACT

The described systems and methods determine a driver's fitness to safely operate a moving vehicle based at least in part upon observed impairment patterns. A smart ring, wearable on a user's finger, continuously monitors impairment levels. This impairment data, representing impairment patterns, can be utilized, in combination with driving data, to train a machine learning model, which will predict the user's level of risk exposure based at least in part upon observed impairment patterns. The user can be warned of this risk to prevent them from driving or to encourage them to delay driving. In some instances, the disclosed smart ring system may interact with the user's vehicle to prevent it from starting while the user is in a state of impairment induced by substance intoxication.

17 Claims, 8 Drawing Sheets

(51) Int. Cl.
*G06N 20/00* (2019.01)
*B60W 50/14* (2020.01)

(52) U.S. Cl.
CPC .............. *B60W 2040/0836* (2013.01); *B60W 2040/0845* (2013.01); *B60W 2040/0872* (2013.01); *B60W 2540/221* (2020.02); *B60W 2540/24* (2013.01); *B60W 2540/26* (2013.01)

(58) Field of Classification Search
CPC . B60W 2040/0845; B60W 2040/0872; B60W 2540/221; B60W 2540/24; B60W 2540/26
See application file for complete search history.

(56) References Cited

U.S. PATENT DOCUMENTS

| | | | |
|---|---|---|---|
| 7,013,674 | B2 | 3/2006 | Kretchmer |
| 7,500,746 | B1 | 3/2009 | Howell et al. |
| 7,872,444 | B2 | 1/2011 | Hamilton et al. |
| 8,446,275 | B2 | 5/2013 | Utter, II |
| 8,570,273 | B1 | 10/2013 | Smith |
| 9,362,775 | B1 | 6/2016 | Jacobs |
| 9,420,260 | B2 | 8/2016 | McGregor et al. |
| 9,477,146 | B2 | 10/2016 | Xu et al. |
| 9,509,170 | B2 | 11/2016 | Wu |
| 9,628,707 | B2 | 4/2017 | Blum et al. |
| 9,660,488 | B2 | 5/2017 | Breedvelt-Schouten et al. |
| 9,696,690 | B2 | 7/2017 | Nguyen et al. |
| 9,711,060 | B1 | 7/2017 | Lusted et al. |
| 9,711,993 | B2 | 7/2017 | Kim |
| 9,717,949 | B1 | 8/2017 | Tran et al. |
| 9,756,301 | B2 | 9/2017 | Li et al. |
| 9,847,020 | B2 | 12/2017 | Davis |
| 9,861,314 | B2 | 1/2018 | Haverinen et al. |
| 9,908,530 | B1 | 3/2018 | Fields et al. |
| 9,955,286 | B2 | 4/2018 | Segal |
| 9,956,963 | B2 | 5/2018 | Kumar et al. |
| 9,965,761 | B2 | 5/2018 | Elangovan et al. |
| 10,007,355 | B2 | 6/2018 | Schorsch et al. |
| 10,085,695 | B2 | 10/2018 | Ouwerkerk et al. |
| 10,099,608 | B2 | 10/2018 | Cuddihy et al. |
| 10,102,510 | B2 | 10/2018 | Yau et al. |
| 10,137,777 | B2 | 11/2018 | Lu et al. |
| 10,317,940 | B2 | 6/2019 | Eim et al. |
| 10,359,846 | B2 | 7/2019 | Priyantha et al. |
| 10,366,220 | B2 | 7/2019 | Shapiro et al. |
| 10,396,584 | B2 | 8/2019 | Madau et al. |
| 10,409,327 | B2 | 9/2019 | Stotler |
| 10,444,834 | B2 | 10/2019 | Vescovi et al. |
| 10,463,141 | B2 | 11/2019 | Fitzgerald et al. |
| 10,629,175 | B2 | 4/2020 | Yan et al. |
| 10,664,842 | B1 | 5/2020 | Bermudez et al. |
| 10,693,872 | B1 | 6/2020 | Larson et al. |
| 10,703,204 | B2 | 7/2020 | Hassan et al. |
| 10,745,032 | B2 | 8/2020 | Scheggi |
| 11,227,060 | B1 | 1/2022 | John et al. |
| 2002/0121831 | A1 | 9/2002 | Egawa et al. |
| 2005/0230596 | A1 | 10/2005 | Howell et al. |
| 2008/0068559 | A1 | 3/2008 | Howell et al. |
| 2008/0218684 | A1 | 9/2008 | Howell et al. |
| 2011/0007035 | A1 | 1/2011 | Shai |
| 2012/0184367 | A1 | 7/2012 | Parrott et al. |
| 2014/0107493 | A1 | 4/2014 | Yuen et al. |
| 2014/0118704 | A1 | 5/2014 | Duelli et al. |
| 2014/0120983 | A1 | 5/2014 | Lam |
| 2014/0218529 | A1 | 8/2014 | Mahmoud et al. |
| 2014/0238153 | A1 | 8/2014 | Wood et al. |
| 2015/0046996 | A1 | 2/2015 | Slaby et al. |
| 2015/0062035 | A1 | 3/2015 | Nattukallingal |
| 2015/0124096 | A1 | 5/2015 | Koravadi |
| 2015/0126824 | A1 | 5/2015 | Leboeuf et al. |
| 2015/0158499 | A1 | 6/2015 | Koravadi |
| 2015/0220109 | A1 | 8/2015 | Von et al. |
| 2015/0277559 | A1 | 10/2015 | Vescovi et al. |
| 2015/0338926 | A1 | 11/2015 | Park et al. |
| 2015/0352953 | A1 | 12/2015 | Koravadi |
| 2016/0028267 | A1 | 1/2016 | Lee et al. |
| 2016/0226313 | A1 | 8/2016 | Okubo |
| 2016/0236692 | A1 | 8/2016 | Kleen et al. |
| 2016/0292563 | A1 | 10/2016 | Park |
| 2016/0317060 | A1 | 11/2016 | Connor |
| 2016/0334901 | A1 | 11/2016 | Rihn |
| 2017/0010677 | A1 | 1/2017 | Roh et al. |
| 2017/0012925 | A1 | 1/2017 | Tekin et al. |
| 2017/0024008 | A1 | 1/2017 | Kienzle et al. |
| 2017/0026790 | A1 | 1/2017 | Flitsch et al. |
| 2017/0042477 | A1 | 2/2017 | Haverinen et al. |
| 2017/0053461 | A1 | 2/2017 | Pal et al. |
| 2017/0070078 | A1 | 3/2017 | Hwang et al. |
| 2017/0075701 | A1 | 3/2017 | Ricci et al. |
| 2017/0080952 | A1 | 3/2017 | Gupta et al. |
| 2017/0090475 | A1 | 3/2017 | Choi et al. |
| 2017/0109512 | A1 | 4/2017 | Bower et al. |
| 2017/0129335 | A1* | 5/2017 | Lu .................... G06F 1/1684 |
| 2017/0131772 | A1 | 5/2017 | Choi |
| 2017/0190121 | A1 | 7/2017 | Aggarwal et al. |
| 2017/0242428 | A1 | 8/2017 | Pal et al. |
| 2017/0346635 | A1 | 11/2017 | Gummeson et al. |
| 2017/0347895 | A1 | 12/2017 | Wei et al. |
| 2017/0374074 | A1 | 12/2017 | Stuntebeck |
| 2018/0025351 | A1 | 1/2018 | Chen et al. |
| 2018/0025430 | A1 | 1/2018 | Perl et al. |
| 2018/0032126 | A1 | 2/2018 | Liu |
| 2018/0037228 | A1 | 2/2018 | Biondo et al. |
| 2018/0039303 | A1 | 2/2018 | Hashimoto et al. |
| 2018/0054513 | A1 | 2/2018 | Ma |
| 2018/0068105 | A1 | 3/2018 | Shapiro et al. |
| 2018/0093606 | A1 | 4/2018 | Terwilliger et al. |
| 2018/0115797 | A1 | 4/2018 | Wexler et al. |
| 2018/0120892 | A1 | 5/2018 | Von et al. |
| 2018/0123629 | A1 | 5/2018 | Wetzig |
| 2018/0167200 | A1 | 6/2018 | High et al. |
| 2018/0174457 | A1* | 6/2018 | Taylor .............. G08G 1/096741 |
| 2018/0292901 | A1 | 10/2018 | Priyantha et al. |
| 2018/0300467 | A1 | 10/2018 | Kwong et al. |
| 2019/0049267 | A1 | 2/2019 | Huang |
| 2019/0083022 | A1 | 3/2019 | Huang |
| 2019/0131812 | A1 | 5/2019 | Lee et al. |
| 2019/0155104 | A1 | 5/2019 | Li et al. |
| 2019/0191998 | A1 | 6/2019 | Heikenfeld et al. |
| 2019/0230507 | A1 | 7/2019 | Li et al. |
| 2019/0265868 | A1 | 8/2019 | Penilla et al. |
| 2019/0286805 | A1 | 9/2019 | Law et al. |
| 2019/0287083 | A1 | 9/2019 | Wurmfeld et al. |
| 2019/0298173 | A1 | 10/2019 | Lawrence et al. |
| 2019/0332140 | A1 | 10/2019 | Wang et al. |
| 2019/0342329 | A1 | 11/2019 | Turgeman |
| 2019/0357834 | A1 | 11/2019 | Aarts et al. |
| 2020/0005791 | A1 | 1/2020 | Rakshit et al. |
| 2020/0070840 | A1* | 3/2020 | Gunaratne ............ B60W 40/09 |
| 2020/0218238 | A1 | 7/2020 | Wang |
| 2020/0356652 | A1 | 11/2020 | Yamaguchi et al. |
| 2020/0391696 | A1 | 12/2020 | Kato et al. |
| 2021/0197849 | A1 | 7/2021 | Tsuji |
| 2021/0382684 | A1 | 12/2021 | Hachiya et al. |
| 2022/0083149 | A1 | 3/2022 | Keller et al. |

FOREIGN PATENT DOCUMENTS

| | | |
|---|---|---|
| CN | 206333477 U | 7/2017 |
| CN | 206371611 U | 8/2017 |
| CN | 107139933 A | 9/2017 |
| CN | 107260139 A | 10/2017 |
| CN | 108900691 A | 11/2018 |
| CN | 108926081 A | 12/2018 |
| DE | 102015006677 A1 | 11/2016 |
| DE | 102019116618 A1 | 12/2020 |
| EP | 2581856 A1 | 4/2013 |
| KR | 10-2017-0087113 A | 7/2017 |
| WO | 2015/077418 A1 | 5/2015 |
| WO | 2017/136940 A1 | 8/2017 |
| WO | 2018/154341 A1 | 8/2018 |
| WO | 2018/204811 A1 | 11/2018 |

(56) References Cited

FOREIGN PATENT DOCUMENTS

| | | |
|---|---|---|
| WO | 2019/082095 A1 | 5/2019 |
| WO | 2019/140528 A1 | 7/2019 |
| WO | 2019/180626 A1 | 9/2019 |

OTHER PUBLICATIONS

"How to find your ideal bedtime with the Oura app", available online at <https://web.archive.org/web/20191206205332/https://ouraring.com/how-to-find-your-ideal-bedtime-with-the-oura-app/> 2019, 8 pages.

"Vauxhall/Opel In-Car Wireless Charging", retrieved from <https://www.air-charge.com/aircharge-for-business/automotive/vauxhall-wireless- charging>, Oct. 2019, 4 pages.

"Wireless charging for smart ring/pointing devices" available online at <http://www.humavox.com/smt_product/wireless-charging-for-smart-ringpointing-devices/>, Oct. 2019, 3 pages.

ASU projection wearable: Live tomorrow today (world first launch @ CES 2016) (Dec. 2015) ASU Tech, YouTube. Retrieved from https://www.youtube.com/watch?v=Wdb50-D7Y0Y.

Brownell, L., "Low-cost wearables manufactured by hybrid 3D printing. Wyss Institute, Harvard," Retrieved from https://wyss.harvard.edu/news/low-cost-wearables-manufactured-by-hybrid-3d-printing/, Sep. 6, 2017, pp. 11.

Cetin, C., "Design, testing and implementation of a new authentication method using multiple devices," Graduate Theses and Dissertations, University of South Florida Scholar Commons. Retrieved from http://scholarcommons.usf.edu/etd/5660, Jan. 2015, pp. 61.

Charles Q. Choi, "Low Battery? New Tech Lets You Wirelessly Share Power", available online at <https://www.livescience.com/54790-new-tech-enables-wireless-charging.html>. May 19, 2016, 9 pages.

Chen, X. A., et al., "Encore: 3D printed augmentation of everyday objects with printed-over, affixed and interlocked attachments," Nov. 5, 2015, pp. 73-82.

Chen, X. A., et al., "Reprise: A design tool for specifying, generating, and customizing 3D printable adaptations on everyday objects," Oct. 16, 2016, pp. 29-39.

E-Senses, "Personal vitamin D, sunlight and daylight coach", available online at <https://e-senses.com/>, 2019, 5 pages.

Hipolite, W., "The 3D printed Ö Bluetooth Ring is one of the tiniest personal computers you will ever see," 3DPrint.com. Retrieved from https://3dprint.com/34627/o-bluetooth-ring-3d-printed/, Jan. 2015, pp. 5.

Hussain Almossawi, "This smart ring aims to provide better lives for people with sickle cell disease", retrieved from <https://www.core77.com/projects/82131/This-Smart-Ring-Aims-to-Provide-Better-Lives-for-People-with-Sickle-Cell-Disease>, 2021, 9 pages.

Je et al., "PokeRing: Notifications by poking around the finger", Proceedings of the 2018 CHI Conference on Human Factors in Computing Systems—CHI'18, 2018, paper 542, pp. 1-10.

Katharine Schwab, "Orii, the ring that turns your finger into a phone, is here", available online at <https://www.fastcompany.com/90399237/orii-the-ring-that-turns-your-finger-into-a-phone-is-here >, 2019, 4 pages.

Magno et al., "Self-sustainable smart ring for long-term monitoring of blood oxygenation", IEEE Access, 2019, pp. 115400-115408.

Mahmud et al., "Wearable technology for drug abuse detection: A survey of recent advancements", Smart Health, vol. 13, Aug. 2019, 100062.

Margaret, "The Orb: A Bluetooth headset that turns into a ring", Gadgets, BornRich, Jun. 2013, available online at <http://www.bornrich.com/the-orb-a-bluetooth-headset-that-turns-into-a-ring.html >.

Nassi et al., "Virtual breathalyzer", Department of Software and Information Systems Engineering, Ben-Gurion University of the Negev, Israel, 2016, 10 pages.

Neev Kiran, "SkinnySensor: Enabling Battery-Less Wearable Sensors Via Intrabody Power Transfer", Masters Theses 694, University of Massachusetts Amherst, 2018, 63 pages.

Nerd-Fu, "Push present", Delicious Juice Dot Com, Apr. 2015, available online at <https://blog.deliciousjuice.com/2015/04/ >.

Pablo E Suárez, "NXT Ring—Your Digital-self at Hand", available online at <https://www.youtube.com/watch?v=9w7uxDHs7NY>, uploaded on Jun. 21, 2019, 2 pages.

Roumen et al., "NotiRing: A comparative study of notification channels for wearable interactive rings", Proceedings of the 33rd Annual ACM Conference on Human Factors in Computing Systems—CHI'15, 2015, pp. 2497-2500.

Sarah Jacobsson Purewal, "Ringly review: The smart ring that could be sexier", available online at <https://www.macworld.com/article/227133/ringly-review-the-smart-ring-that-could-be-sexier.html>, 2016, 10 pages.

Schwab, K., "This startup wants to kill passwords-and replace them with jewelry. Fast Company," Retrieved from https://www.fastcompany.com/90254843/this-startup-wants-to-kill-passwords-and-replace-them-with-jewelry, (Oct. 2018), pp. 7.

Seung et al., "Nanopatterned Textile-Based Wearable Triboelectric Nanogenerator", ACS Nano, vol. 9, 2015, pp. 3501-3509.

Shane McGlaun, "Geek builds Bluetooth Smart Ring with OLED display", available online at <https://www.slashgear.com/geek-builds-bluetooth-smart-ring-with-oled-display-02361383/>, 2015, 6 pages.

Sperlazza, "We tested four sleep tracker apps and wearables: Here are the best ones", available online at <https://www.bulletproof.com/sleep/tech/best-sleep-tracker-apps/>, 2019, 18 pages.

Turunen, "Smart ring for stress control and self-understanding", available online at <https://slowfinland.fi/en/smart-ring-for-stress-control-and-self-understanding/>, 2017, 9 pages.

Wochit Tech. (2017). New smart ring monitors UV exposure [Video file]. Retrieved from https://www.youtube.com/watch?v=4YvkioTZxjU, 3 pages.

Worgan et al., "Garment level power distribution for wearables using inductive power transfer", 9th International Conference on Human System Interactions (HSI), 2016, pp. 277-283.

Xiao et al., "LumiWatch: On-arm projected graphics and touch input", Proceedings of the 2018 CHI Conference on Human Factors in Computing Systems—CHI'18, 2018, pp. 1-11.

Zhu et al., "Developing a driving fatigue detection system using physiological sensors", Proceedings of the 29th Australian Conference on Computer-Human Interaction—OZCHI '17, 2017, pp. 566-570.

Zhu, M. et al. "Fluidic fabric muscle sheets for wearable and soft robotics," Retrieved from https://arxiv.org/pdf/1903.08253.pdf, Mar. 2019, pp. 32.

https://en.wikipedia.org/w/index.php?title=Ring_size&oldid=891328817 (Year: 2019).

Mario, https://www.smartringnews.com/posts/smart-ring-vs-smartwatch-which-is-the-best-fitness-and-activity-tracker (Year: 2014).

Laput et al., "Skin buttons: cheap, small, low-powered and clickable fixed-icon laser projectors", UIST '14: Proceedings of the 27th annual ACM symposium on User interface software and technology, Oct. 2014 pp. 389-394.

Google translation of KR20170087113A (Year: 2016).

* cited by examiner

SMART RING SYSTEM FOR MEASURING DRIVER IMPAIRMENT LEVELS AND USING MACHINE LEARNING TECHNIQUES TO PREDICT HIGH RISK DRIVING BEHAVIOR

CROSS-REFERENCES TO RELATED APPLICATIONS

This application claims priority to U.S. Provisional Patent Application No. 62/877,391, filed Jul. 23, 2019, incorporated by reference herein for all purposes.

FIELD OF DISCLOSURE

The present disclosure generally relates to implementations of smart ring wearable devices and, more particularly, to utilizing a smart ring for predicting a driver's fitness to safely operate a moving vehicle based at least in part upon observed impairment patterns.

BACKGROUND

Driving while impaired by an intoxicating substance, legal or illegal, is a road hazard that results in a grave number of injuries and lost lives. Intoxicated drivers endanger themselves and others on the road because their alertness, coordination, judgement, and reaction time may be compromised.

Some drivers have the best intentions to avoid operating a vehicle while impaired to a degree of becoming a safety threat to themselves and those around them, however it can be difficult to correlate the amount and type of a consumed intoxicating substance with its effect on driving abilities. Notably, some people may suffer severe impairment even when staying below legal intoxication limits and may not realize the degree of risk they are exposing themselves to at those low levels of intoxication. The severity of impairment can be a variable of many factors, such as individual metabolism rate, blood pressure, fatigue, diet, and many other personal and environmental factors. The effects and severity of impairment induced by intoxication can vary not only between individuals, but also from one day to another for the same person due to a variety of transient factors. Further, in some instances, the intoxicating substance might alter the user's consciousness and prevent them from making a rational decision on their own about whether they are fit to operate a vehicle.

There is a need for discrete systems for self-assessing the severity of impairment induced by intoxicating substances and making a prediction of the effects of that impairment on driving safety.

BRIEF SUMMARY

The present disclosure relates to a smart wearable ring system and methods that allow for continuous monitoring of the user's levels of impairment due to intoxication and using that data to determine a ring wearer's fitness to safely operate a moving vehicle.

More specifically, the disclosed smart ring collects impairment data representing impairment patterns. This impairment data can be utilized, in combination with driving data, as training data for a machine learning (ML) model to train the ML model to predict high risk driving based at least in part upon observed impairment patterns (e.g., patterns relating to a person's motor functions, such as a gait; patterns of sweat composition that may reflect intoxication; patterns regarding a person's vitals; etc.). A user can be warned of this risk to prevent them from driving or to encourage them to delay driving. In some instances, the disclosed smart ring system may interact with the user's vehicle to prevent it from starting while the user is in an impaired state caused by substance intoxication.

Presently, there are no conventional technologies capable of discretely assessing in real time driver impairment and risk exposure induced by substance intoxication. The conventional focus in the field is on detecting the presence of such impairing substances in one's system, and for some of the legal ones—comparing the detected levels to the allowed generalized thresholds, determined as biological matrix concentration levels under which an average person can safely operate a moving vehicle. The present technologies typically test for the presence of intoxicating substances in one's system by analyzing breath, blood, or urine. Blood and urine analysis is typically performed in a laboratory, which hinders rapid quantification, let alone being determined by individuals themselves, with self-testing devices or sensors. The conventional portable field devices known as breathalyzers, can analyze the concentration of intoxicating substances in a subject's breath. Even in a miniature form, breathalyzers cannot be applied discreetly.

Some users might not want to admit socially to using devices like breathalyzers that assist them in tracking their own intoxication levels. These devices also rely on the user remembering to use such a device. The form factor of the disclosed smart ring improves on conventional field devices for estimating blood drug content from a breath sample by enabling inconspicuous and convenient data collection in real time. A monitoring device disguised as a ring solves this issue, making the ring more conducive for continuous wear and use.

In an embodiment, an inconspicuous and comfortable ring-shaped device, intended to be worn on a user's hand, is outfitted with sensors that are able to collect the ring user's specific biochemical, physiological, and motion parameters indicative of patterns corresponding to impairment induced by intoxication. A system trains and implements a Machine Learning (ML) algorithm to make a personalized prediction of the level of driving risk exposure based at least in part upon the captured impairment data. The ML model training may be achieved, for example, at a server by first (i) acquiring, via a smart ring, one or more sets of first data indicative of one or more impairment patterns; (ii) acquiring, via a driving monitor device, one or more sets of second data indicative of one or more driving patterns; (iii) utilizing the one or more sets of first data and the one or more sets of second data as training data for a ML model to train the ML model to discover one or more relationships between the one or more impairment patterns and the one or more driving patterns, wherein the one or more relationships include a relationship representing a correlation between a given impairment pattern and a high-risk driving pattern.

The impairment data may include physiological data, such as data on the user's vital signs: blood pressure, heart rate, body temperature, and data on skin conductance and skin perfusion. The impairment data may additionally or alternatively include motion data, capturing the user's gait patterns characteristic of a person under the influence of an intoxicating substance, such as swaying, tripping, falling, dragging, skipping, walking sideways, or walking with support, etc. The impairment data may additionally or alternatively include the user's biochemical parameters, which are determined from the analysis of sweat concentration of the monitored intoxicating substances.

Sweat has been demonstrated as a suitable biological matrix for monitoring recent drug use. Sweat monitoring for intoxicating substances is based at least in part upon the assumption that, in the context of the absorption-distribution-metabolism-excretion (ADME) cycle of drugs, a small but sufficient fraction of lipid-soluble consumed substances pass from blood plasma to sweat. These substances are incorporated into sweat by passive diffusion towards a lower concentration gradient, where a fraction of compounds unbound to proteins cross the lipid membranes. Furthermore, since sweat, under normal conditions, is slightly more acidic than blood, basic drugs tend to accumulate in sweat, aided by their affinity towards a more acidic environment.

In an embodiment, the trained ML model analyzes a particular set of data collected by a particular smart ring associated with a user, and (i) determines that the particular set of data represents a particular impairment pattern corresponding to the given impairment pattern correlated with the high-risk driving pattern; and (ii) responds to said determining by predicting a level of risk exposure for the user during driving.

The method may further include: (i) predicting a level of driving risk exposure to a driver based at least in part upon analyzed impairment patterns; and (ii) communicating the predicted risk exposure; and (iii) determining remediating action to reduce or eliminate the driving risk; or communicate or implement the remediating action in accordance with various embodiments disclosed herein. The described determinations regarding remediation may be made prior to the ring user attempting driving, thereby enabling the smart ring and any associated systems to prevent or discourage the user from driving while exposed to high risk caused by deteriorated cognitive or physiological functions stemming from impairment due to substance intoxication.

Depending upon the embodiment, one or more benefits may be achieved. These benefits and various additional objects, features and advantages of the present disclosure can be fully appreciated with reference to the detailed description and accompanying drawings that follow.

DETAILED DESCRIPTION

FIG. 1, FIG. 2, FIG. 3, FIG. 4, FIG. 5, FIG. 6, FIG. 7, and FIG. 8 discuss various techniques, systems, and methods for implementing a smart ring to train and implement a machine learning module capable of predicting a driver's risk exposure based at least in part upon observed impairment patterns. Specifically, sections I, II, III and V describe, with reference to FIG. 1, FIG. 2, FIG. 4, and FIG. 6, example smart ring systems, form factor types, and components. Section IV describes, with reference to FIG. 4, an example smart ring environment. Sections VI and VII describe, with reference to FIG. 6 and FIG. 7, example methods that may be implemented via the smart ring systems described herein. And Section VIII describes, with reference to FIG. 8, example elements of a vehicle that may communicate with one of the described smart ring systems to facilitate implementation of the functions described herein.

I. Examples of Smart Ring and Smart Ring Components

Figure 1:
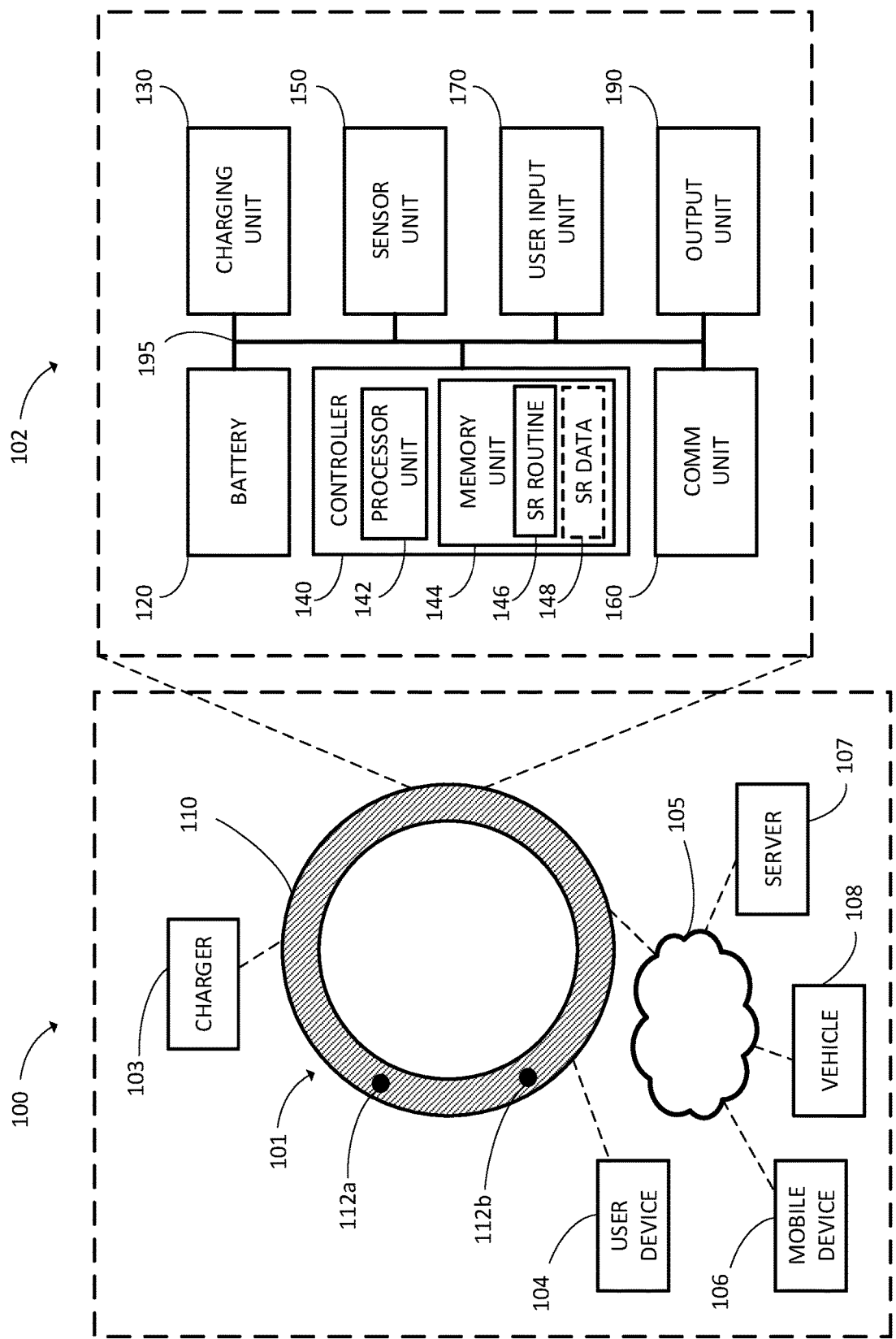
FIG. 1 illustrates a system comprising a smart ring and a block diagram of smart ring components.

FIG. 1 illustrates a smart ring system 100 for predicting a level of driving risk exposure to a driver based at least in part upon one or more analyzed impairment patterns, comprising (i) a smart ring 101 including a set of components 102 and (ii) one or more devices or systems that may be electrically, mechanically, or communicatively connected to the smart ring 101, according to an embodiment. Specifically, the system 100 may include any one or more of: a charger 103 for the smart ring 101, a user device 104, a network 105, a mobile device 106, a vehicle 108, or a server 107. The charger 103 may provide energy to the smart ring 101 by way of a direct electrical, a wireless, or an optical connection. The smart ring 101 may be in a direct communicative connection with the user device 104, the mobile device 106, the server 107, or a vehicle 108 by way of the network 105. Interactions between the smart ring 101 and other components of the system 100 are discussed in more detail in the context of FIG. 4.

The smart ring 101 may sense a variety of signals indicative of: activities of a user wearing the ring 101, measurements of physiological parameters of the user, or aspects of the user's environment. The smart ring 101 may analyze the sensed signals using built-in computing capabilities or in cooperation with other computing devices (e.g., user device 104, mobile device 106, server 107, or vehicle 108) and provide feedback to the user or about the user via the smart ring 101 or other devices (e.g., user device 104, mobile device 106, server 107, or vehicle 108). Additionally or alternatively, the smart ring 101 may provide the user with notifications sent by other devices, enable secure access to locations or information, or a variety of other applications pertaining to health, wellness, productivity, or entertainment. While some figures and select embodiment descriptions refer to a vehicle in the form of an automobile, the technology is not limited to communicating with automotive vehicles. That is, references to a "vehicle" may be understood as referring to any human-operated transportation device or system, such as a train, aircraft, watercraft, submersible, spacecraft, cargo truck, recreational vehicle, agricultural machinery, powered industrial truck, bicycle, motorcycle, hovercraft, etc.

The smart ring 101, which may be referred to herein as the ring 101, may comprise a variety of mechanical, electrical, electrochemical, optical, or any other suitable subsystems, devices, components, or parts disposed within, at, throughout, or in mechanical connection to a housing 110 (which may be ring shaped and generally configured to be worn on a finger). Additionally, a set of interface components 112a and 112b may be disposed at the housing, and, in particular, through the surface of the housing. The interface components 112a and 112b may provide a physical access (e.g., electrical, fluidic, mechanical, or optical) to the components disposed within the housing. The interface components 112a and 112*b* may exemplify surface elements disposed at the housing. As discussed below, some of the surface elements of the housing may also be parts of the smart ring components.

As shown in FIG. 1, the components 102 of the smart ring 101 may be distributed within, throughout, or on the housing 110. As discussed in the contexts of FIG. 2 and FIG. 3 below, the housing 110 may be configured in a variety of ways and include multiple parts. The smart ring components 102, for example, may be distributed among the different parts of the housing 110, as described below, and may include surface elements of the housing 110. The housing 110 may include mechanical, electrical, optical, electrochemical, or any other suitable subsystems, devices, components, or parts disposed within or in mechanical connection to the housing 110, including a battery 120, a charging unit 130, a controller 140, a sensor system 150 comprising one or more sensors, a communications unit 160, one or more user input devices 170, or one or more output devices 190. Each of the components 120, 130, 140, 150, 160, 170, and/or 190 may include one or more associated circuits, as well as packaging elements. The components 120, 130, 140, 150, 160, 170, and/or 190 may be electrically or communicatively connected with each other (e.g., via one or more busses or links, power lines, etc.), and may cooperate to enable "smart" functionality described within this disclosure.

The battery 120 may supply energy or power to the controller 140, the sensors 150, the communications unit 160, the user input devices 170, or the output devices 190. In some scenarios or implementations, the battery 120 may supply energy or power to the charging unit 130. The charging unit 130, may supply energy or power to the battery 120. In some implementations, the charging unit 130 may supply (e.g., from the charger 103, or harvested from other sources) energy or power to the controller 140, the sensors 150, the communications unit 160, the user input devices 170, or the output devices 190. In a charging mode of operation of the smart ring 101, the average power supplied by the charging unit 130 to the battery 120 may exceed the average power supplied by the battery 120 to the charging unit 130, resulting in a net transfer of energy from the charging unit 130 to the battery 120. In a non-charging mode of operation, the charging unit 130 may, on average, draw energy from the battery 120.

The battery 120 may include one or more cells that convert chemical, thermal, nuclear or another suitable form of energy into electrical energy to power other components or subsystems 140, 150, 160, 170, and/or 190 of the smart ring 101. The battery 120 may include one or more alkaline, lithium, lithium-ion and or other suitable cells. The battery 120 may include two terminals that, in operation, maintain a substantially fixed voltage of 1.5, 3, 4.5, 6, 9, 12 V or any other suitable terminal voltage between them. When fully charged, the battery 120 may be capable of delivering to power-sinking components an amount of charge, referred to herein as "full charge," without recharging. The full charge of the battery may be 1, 2, 5, 10, 20, 50, 100, 200, 500, 1000, 2000, 5000, 10000, 20000 mAh or any other suitable charge that can be delivered to one or more power-consuming loads as electrical current.

The battery 120 may include a charge-storage device, such as, for example a capacitor or a super-capacitor. In some implementations discussed below, the battery 120 may be entirely composed of one or more capacitive or charge-storage elements. The charge storage device may be capable of delivering higher currents than the energy-conversion cells included in the battery 120. Furthermore, the charge storage device may maintain voltage available to the components or subsystems 130, 140, 150, 160, 170, and/or 190 when one or more cells of the battery 120 are removed to be subsequently replaced by other cells.

The charging unit 130 may be configured to replenish the charge supplied by the battery 120 to power-sinking components or subsystems (e.g., one or more of subsystems 130, 140, 150, 160, 170, and/or 190) or, more specifically, by their associated circuits. To replenish the battery charge, the charging unit 130 may convert one form of electrical energy into another form of electrical energy. More specifically, the charging unit 130 may convert alternating current (AC) to direct current (DC), may perform frequency conversions of current or voltage waveforms, or may convert energy stored in static electric fields or static magnetic fields into direct current. Additionally or alternatively, the charging unit 130 may harvest energy from radiating or evanescent electromagnetic fields (including optical radiation) and convert it into the charge stored in the battery 120. Furthermore, the charging unit 130 may convert non-electrical energy into electrical energy. For example, the charging unit 130 may harvest energy from motion, or from thermal gradients.

The controller 140 may include a processor unit 142 and a memory unit 144. The processor unit 142 may include one or more processors, such as a microprocessor (μP), a digital signal processor (DSP), a central processing unit (CPU), a graphical processing unit (GPU), a field-programmable gate array (FPGA), an application-specific integrated circuit (ASIC), or any other suitable electronic processing components. Additionally or alternatively, the processor unit 142 may include photonic processing components.

The memory unit 144 may include one or more computer memory devices or components, such as one or more registers, RAM, ROM, EEPROM, or on-board flash memory. The memory unit 144 may use magnetic, optical, electronic, spintronic, or any other suitable storage technology. In some implementations, at least some of the functionality the memory unit 144 may be integrated in an ASIC or and FPGA. Furthermore, the memory unit 144 may be integrated into the same chip as the processor unit 142 and the chip, in some implementations, may be an ASIC or an FPGA.

The memory unit 144 may store a smart ring (SR) routine 146 with a set of instructions, that, when executed by the processor 142 may enable the operation and the functionality described in more detail below. Furthermore, the memory unit 144 may store smart ring (SR) data 148, which may include (i) input data used by one or more of the components 102 (e.g., by the controller when implementing the SR routine 146) or (ii) output data generated by one or more of the components 102 (e.g., the controller 140, the sensor unit 150, the communication unit 160, or the user input unit 170). In some implementations, other units, components, or devices may generate data (e.g., diagnostic data) for storing in the memory unit 144.

The processing unit 142 may draw power from the battery 120 (or directly from the charging unit 130) to read from the memory unit 144 and to execute instructions contained in the smart ring routine 146. Likewise, the memory unit 144 may draw power from the battery 120 (or directly from the charging unit 130) to maintain the stored data or to enable reading or writing data into the memory unit 144. The processor unit 142, the memory unit 144, or the controller 140 as a whole may be capable of operating in one or more low-power mode. One such low power mode may maintain the machine state of the controller 140 when less than a threshold power is available from the battery 120 or during a charging operation in which one or more battery cells are exchanged.

The controller 140 may receive and process data from the sensors 150, the communications unit 160, or the user input devices 170. The controller 140 may perform computations to generate new data, signals, or information. The controller 140 may send data from the memory unit 144 or the generated data to the communication unit 160 or the output devices 190. The electrical signals or waveforms generated by the controller 140 may include digital or analog signals or waveforms. The controller 140 may include electrical or electronic circuits for detecting, transforming (e.g., linearly or non-linearly filtering, amplifying, attenuating), or converting (e.g., digital to analog, analog to digital, rectifying, changing frequency) of analog or digital electrical signals or waveforms.

In various embodiments, the sensor unit 150 may include one or more sensors disposed within or throughout the housing 110 of the ring 101. Each of the one or more sensors may transduce one or more of: light, sound, acceleration, translational or rotational movement, strain, pressure, temperature, chemical composition, surface conductivity or other suitable signals into electrical or electronic sensors or signals. The one or more sensors may be acoustic, photonic, micro-electro-mechanical systems (MEMS) sensors, chemical, electrochemical, micro-fluidic (e.g., flow sensor), or any other suitable type of sensor. The sensor unit 150 may include, for example, one or more of three-axis accelerometers for detecting orientation and movement of the ring 101. The sensor unit 150 may alternatively or additionally include an inertial measurement unit (IMU) for detecting orientation and movement of the ring 101, such as one having one or more accelerometers and/or altimeters. Such sensors may be employed to capture the user's gait patterns to monitor for characteristic gait patterns indicative of a person under the influence of an intoxicating substance, such as swaying, tripping, falling, dragging, skipping, walking sideways, or walking with support, etc. The sensor unit 150 may include, for example, electrochemical or biochemical sensors, or sensors capable of performing an immunochromatographic test of a sample, which may be further integrated with microfluidic devices to monitor the levels of intoxicating substances in sweat, substances such as alcohol, THC, opioids, cocaine, MDMA, amphetamines, ketamine, phencyclidine, GHB, and/or other legal or illegal substances known to impair an individual's cognitive or physiological functions. The one or more sensors of the sensor unit 150 may provide data indicative, but not limiting to, the user's heart rate (HR), blood pressure, body temperature, skin conductance, skin perfusion, hand grip and/or strain, gait, body motion data, vehicular motion data (when the ring user is positioned inside of a moving vehicle), gesticulation, the amount of sweat and its composition, speech recognition, and sunlight and/or UV radiation exposure. The sensor unit 150 may also be equipped with a Global Positioning System (GPS) receiver.

The communication unit 160 may facilitate wired or wireless communication between the ring 101 and one or more other devices. The communication unit 160 may include, for example, a network adaptor to connect to a computer network, and, via the network, to network-connected devices. The computer network may be the Internet or another type of suitable network (e.g., a personal area network (PAN), a local area network (LAN), a metropolitan area network (MAN), a wide area network (WAN), a mobile, a wired or wireless network, a private network, a virtual private network, etc.). The communication unit 160 may use one or more wireless protocols, standards, or technologies for communication, such as Wi-Fi, near field communication (NFC), Bluetooth, or Bluetooth low energy (BLE). Additionally or alternatively, the communication unit 160 may enable free-space optical or acoustic links. In some implementations, the communication unit 160 may include one or more ports for a wired communication connection. The wired connections used by the wireless communication module 160 may include electrical or optical connections (e.g., fiber-optic, twisted-pair, coaxial cable).

User input unit 170 may collect information from a person wearing the ring 101 or another user, capable of interacting with the ring 101. In some implementations, one or more of the sensors in the sensor unit 150 may act as user input devices within the user input unit 170. User input devices may transduce tactile, acoustic, video, gesture, or any other suitable user input into digital or analog electrical signal and send these electrical signals to the controller 140.

The output unit 190 may include one or more devices to output information to a user of the ring 101. The one or more output devices may include acoustic devices (e.g., speaker, ultrasonic); haptic, thermal, electrical devices; electronic displays for optical output, such as an organic light emitting device (OLED) display, a laser unit, a high-power light-emitting device (LED), etc.; or any other suitable types of devices. For example, the output unit 190 may include a projector that projects an image onto a suitable surface. In some implementations, the sensor unit 150, the user input unit 170, and the output unit 190 may cooperate to create a user interface with capabilities (e.g., a keyboard) of much larger computer systems, as described in more detail below.

The components 120, 130, 140, 150, 160, 170, and/or 190 may be interconnected by a bus (not shown), which may be implemented using one or more circuit board traces, wires, or other electrical, optoelectronic, or optical connections. The bus may be a collection of electrical power or communicative interconnections. The communicative interconnections may be configured to carry signals that conform to any one or more of a variety of protocols, such as I2C, SPI, or other logic to enable cooperation of the various components.

II. Example Smart Ring Form Factor Types

Figure 2:
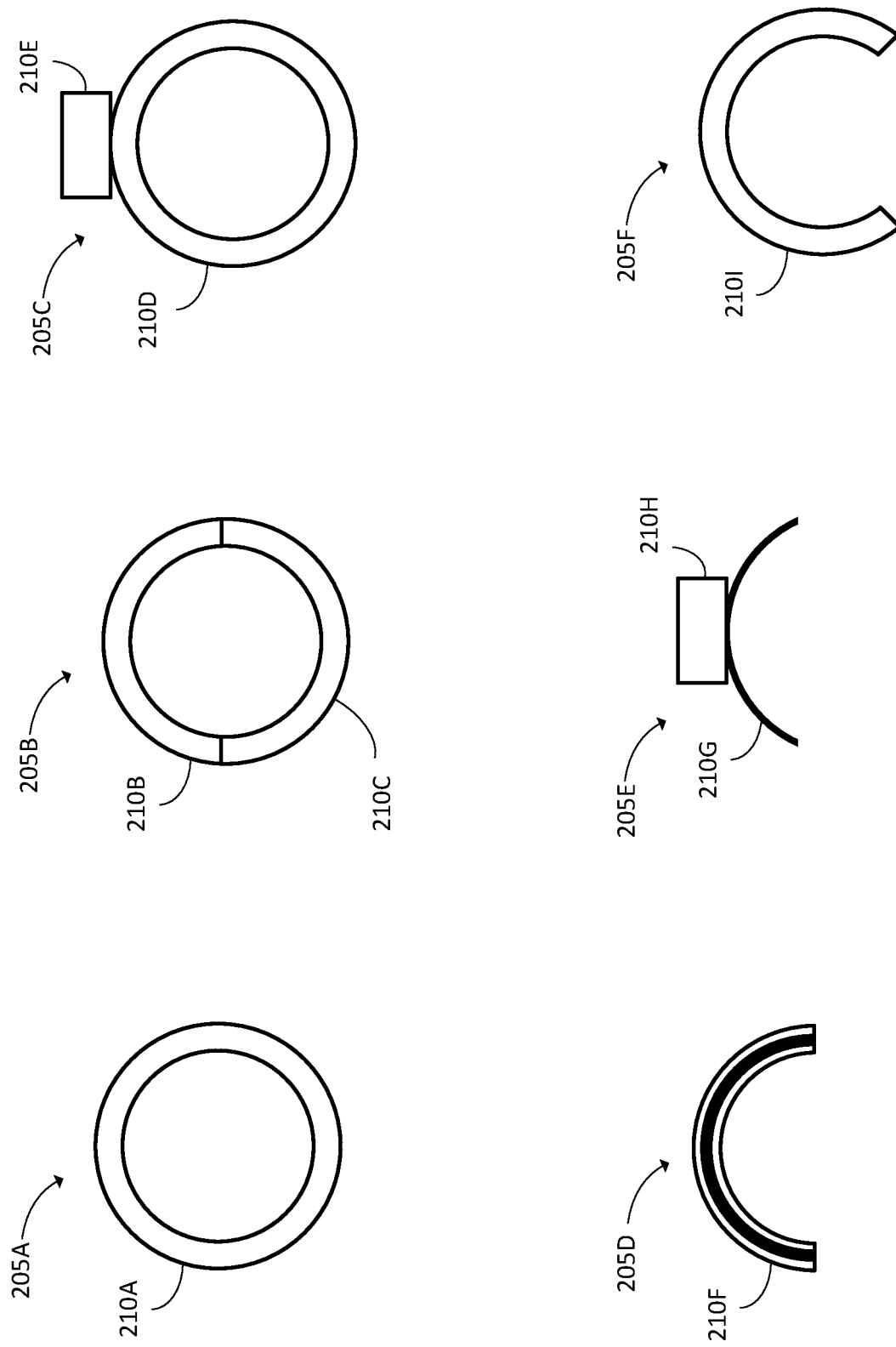
FIG. 2 illustrates a number of different form factor types of a smart ring.

FIG. 2 includes block diagrams of a number of different example form factor types or configurations 205a, 205b, 205c, 205d, 205e, and/or 205f of a smart ring (e.g., the smart ring 101). The configurations 205a, 205b, 205c, 205d, 205e, and/or 205f (which may also be referred to as the smart rings 205a, 205b, 205c, 205d, 205e, and/or 205f) may each represent an implementation of the smart ring 101, and each may include any one or more of the components 102 (or components similar to the components 102). In some embodiments, one or more of the components 102 may not be included in the configurations 205a, 205b, 205c, 205d, 205e, and/or 205f. The configurations 205a, 205b, 205c, 205d, 205e, and/or 205f include housings 210a, 210b, 210c, 210d, 210e, and/or 210f, which may be similar to the housing 110 shown in FIG. 1.

The configuration 205a may be referred to as a band-only configuration comprising a housing 210a. In the configuration 205b, a band may include two or more removably connected parts, such as the housing parts 210b and 210c. The band may also have an inner diameter ranging between 13 mm and 23 mm. The two housing parts 210b and 210c may each house at least some of the components 102, distributed between the housing parks 210b and 210c in any suitable manner.

The configuration 205c may be referred to as a band-and-platform configuration comprising (i) a housing component 210d and (ii) a housing component 210e (sometimes called the "platform 210e"), which may be in a fixed or removable mechanical connection with the housing 210d. The platform 210e may function as a mount for a "jewel" or for any other suitable attachment. The housing component 210d and the platform 210e may each house at least one or more of the components 102 (or similar components).

In some instances, the term "smart ring" may refer to a partial ring that houses one or more components (e.g., components 102) that enable the smart ring functionality described herein. The configurations 205d and 205e may be characterized as "partial" smart rings and may be configured for attachment to a second ring. The second ring may be a conventional ring without smart functionality, or may be a second smart ring, wherein some smart functionality of the first or second rings may be enhanced by the attachment.

The configuration 205d, for example, may include a housing 210f with a groove to enable clipping onto a conventional ring. The grooved clip-on housing 210f may house the smart ring components described above. The configuration 205e may clip onto a conventional ring using a substantially flat clip 210g part of the housing and contain the smart ring components in a platform 210h part of the housing.

The configuration 205f, on the other hand, may be configured to be capable of being mounted onto a finger of a user without additional support (e.g., another ring). To that end, the housing 210i of the configuration 205f may be substantially of a partial annular shape subtending between 180 and 360 degrees of a full circumference. When implemented as a partial annular shape, the housing 210i may be more adaptable to fingers of different sizes that a fully annular band (360 degrees) and may be elastic. A restorative force produced by a deformation of the housing 210i may ensure a suitable physical contact with the finger. Additional suitable combinations of configurations (not illustrated) may combine at least some of the housing features discussed above.

III. Example Smart Ring Surface Elements

Figure 3:
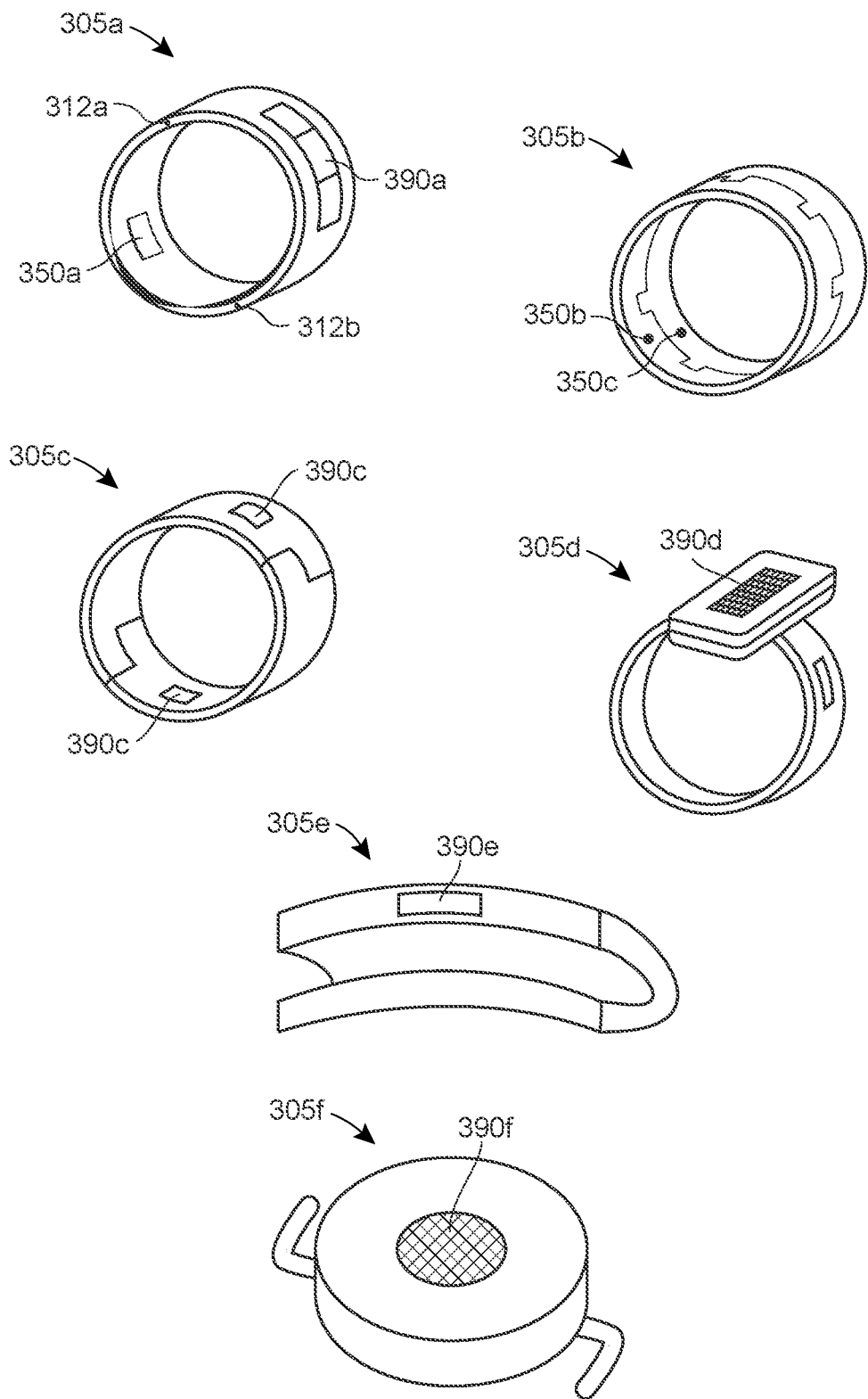
FIG. 3 illustrates examples of different smart ring surface elements.

FIG. 3 includes perspective views of example configurations 305a, 305b, 305c, 305d, 305e, and/or 305f of a smart right (e.g., the smart ring 101) in which a number of surface elements are included.

Configuration 305a is an example band configuration 205a of a smart ring (e.g., smart ring 101). Some of the surface elements of the housing may include interfaces 312a and 312b that may be electrically connected to, for example, the charging unit 130 or the communications unit 160. On the outside of the configuration 305a, the interfaces 312a and 312b may be electrically or optically connected with a charger to transfer energy from the charger to a battery (e.g., the battery 120), or with another device to transfer data to or from the ring 305a. The outer surface of the configuration 305a may include a display 390a, while the inner surface may include a biometric sensor 350a.

The configurations 305b and 305c are examples of configurations of a smart ring with multiple housing parts (e.g., configuration 205b in FIG. 2). Two (or more) parts may be separate axially (configuration 305b), azimuthally (configuration 305c), or radially (nested rings, not shown). The parts may be connected mechanically, electrically, or optically via, for example, interfaces analogous to interfaces 312a and 312b in configuration 305a. Each part of a smart ring housing may have one or more surface elements, such as, for example, sensors 350b and 350c or output elements 390b and 390c. The latter may be LEDs (e.g., output element 390b) or haptic feedback devices (e.g., output element 390c), among other suitable sensor or output devices. Additionally or alternatively, at least some of the surface elements (e.g., microphones, touch sensors) may belong to the user input unit 170.

Configuration 305d may be an example of a band and platform configuration (e.g., configuration 205c), while configurations 305e and 305f may be examples of the partial ring configurations 205d and 205e, respectively. Output devices 390d, 390e, and 390f on the corresponding configurations 305d, 305e, and/or 305f may be LCD display, OLED displays, e-ink displays, one or more LED pixels, speakers, or any other suitable output devices that may be a part of a suite of outputs represented by an output unit (e.g., output unit 190). Other surface elements, such as an interface component 312c may be disposed within, at, or through the housing. It should be appreciated that a variety of suitable surface elements may be disposed at the illustrated configurations 305a, 305b, 305c, 305d, 305e, and/or 305f at largely interchangeable locations. For example, the output elements 390d, 390e, and 390f may be replaced with sensors (e.g., UV sensor, ambient light or noise sensors, etc.), user input devices (e.g., buttons, microphones, etc.), interfaces (e.g., including patch antennas or optoelectronic components communicatively connected to communications units), or other suitable surface elements.

IV. Example Environments for Smart Ring Operation

Figure 4:
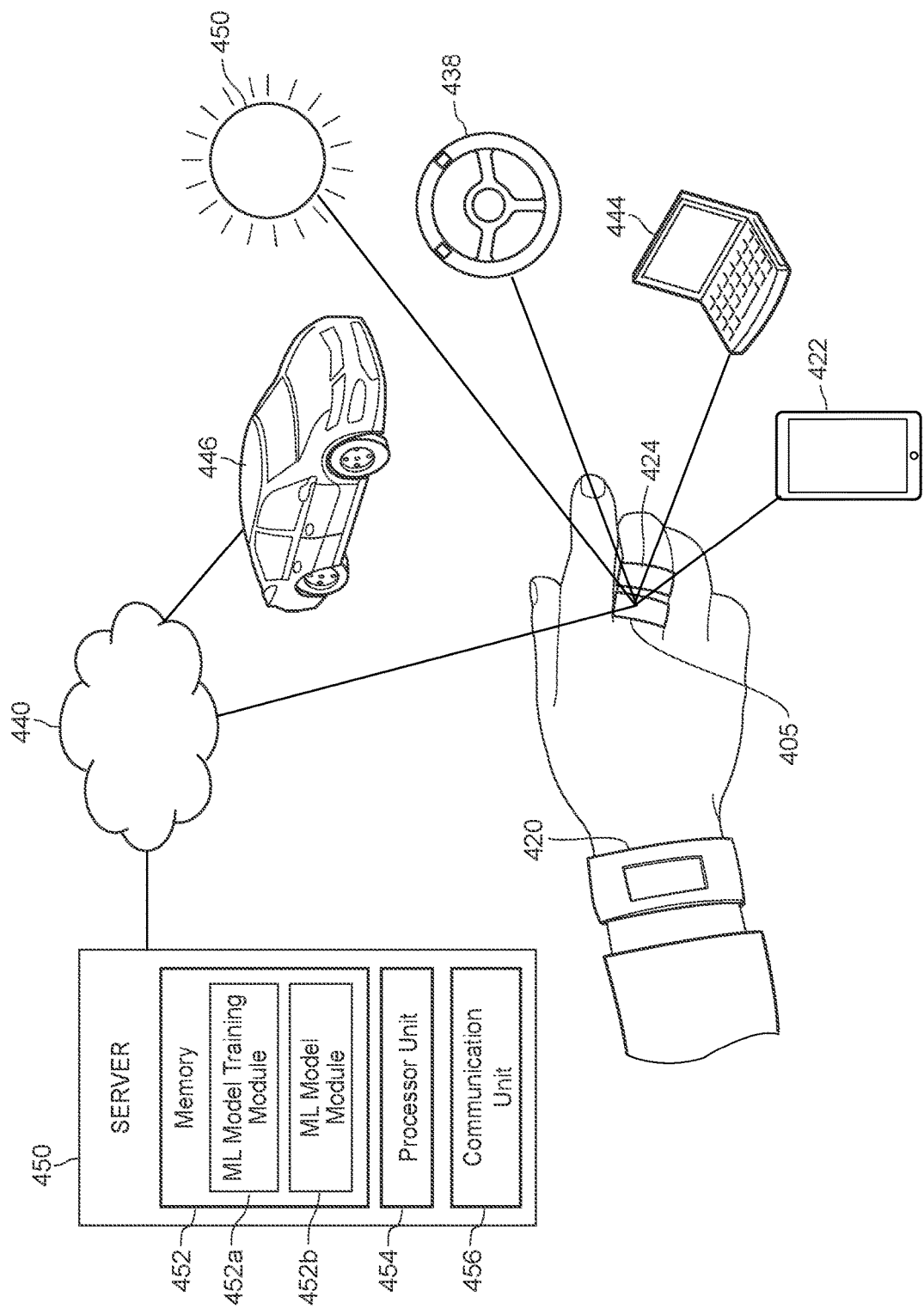
FIG. 4 illustrates example environments for smart ring operation.

FIG. 4 illustrates an example environment 400 within which a smart ring 405 may be configured to operate. In an embodiment, the smart ring 405 may be the smart ring 101. In some embodiments, the smart ring 405 may be any suitable smart ring capable of providing at least some of the functionality described herein. Depending on the embodiment, the smart ring 405 may be configured in a manner similar or equivalent to any of the configurations 205a, 205b, 205c, 205d, 205e, and/or 205f or 305a, 305b, 305c, 305d, 305e, and/or 305f shown in FIG. 2 and FIG. 3.

The smart ring 405 may interact (e.g., by sensing, sending data, receiving data, receiving energy) with a variety of devices, such as bracelet 420 or another suitable wearable device, a mobile device 422 (e.g., a smart phone, a tablet, etc.) that may be, for example, the user device 104, another ring 424 (e.g., another smart ring, a charger for the smart ring 405, etc.), or a steering wheel 438 (or another vehicle interface). Additionally or alternatively, the smart ring 405 may be communicatively connected to a network 440 (e.g., Wifi, 5G cellular), and by way of the network 440 (e.g., network 105 in FIG. 1) to a server 450 (e.g., server 107 in FIG. 1), a personal computer 444 (e.g., mobile device 106), or a vehicle 446 (which may be the vehicle 108). Additionally or alternatively, the ring 405 may be configured to sense or harvest energy from natural environment, such as the sun 450.

A. Example of Server 450

The server 450 is an electronic computing device including at least one non-transitory computer-readable memory 452 storing instructions executable on a processor unit 454, and a communication unit 456, each of which may be communicatively connected to a system bus (not shown) of the server 450. In some instances, the described functionality of the server 450 may be provided by a plurality of servers similar to the server 450. The memory 452 of the server 450 includes a Machine Learning (ML) model training module 452a, and a ML model module 452b, which are a set of machine readable instructions (e.g., a software module, application, or routine). In some embodiments, the server 450 can function as a database to store data utilized by the ML modules 452a and 452b, as well as the model results.

At a high level, the ML model 452b is configured to predict the user's level of driving risk exposure based at least in part upon the user's impairment data, and the ML training module 452a is configured to train the model module 452b with the user's impairment data in combination with driving data. The Machine Learning model modules 452a and 452b are described in greater detail in FIG. 6 below.

B. Example of Ring Communicating with Other Devices

The ring 405 may exchange data with other devices by communicatively connecting to the other devices using, for example, the communication unit 160. The communicative connection to other device may be scheduled, initiated by the ring 405 in response to user input via the user input unit 170, in response to detecting trigger conditions using the sensor unit 150, or may be initiated by the other devices. The communicative connection may be wireless, wired electrical connection, or optical. In some implementation, establishing a communicative link may include establishing a mechanical connection.

The ring 405 may connect to other devices (e.g., a device with the built-in charger 103) to charge the battery 120. The connection to other devices for charging may enable the ring 405 to be recharged without the need for removing the ring 405 from the finger. For example, the bracelet 420 may include an energy source that may transfer the energy from the energy source to battery 120 of the ring 405 via the charging unit 130. To that end, an electrical (or optical) cable may extend from the bracelet 420 to an interface (e.g., interfaces 112a and 112b, 312a and 312b) disposed at the housing (e.g., housings 110, 210a, 210b, 210c, 210d, 210e, 210f, 210g, 210h, and/or 210i) of the ring 405. The mobile device 422, the ring 424, the steering wheel 438 may also include energy source configured as chargers (e.g., the charger 103) for the ring 405. The chargers may transfer energy to the ring 405 via a wired or wireless (e.g., inductive coupling) connection with the charging unit 130 of the ring 405.

V. Example Displays

Figure 5:
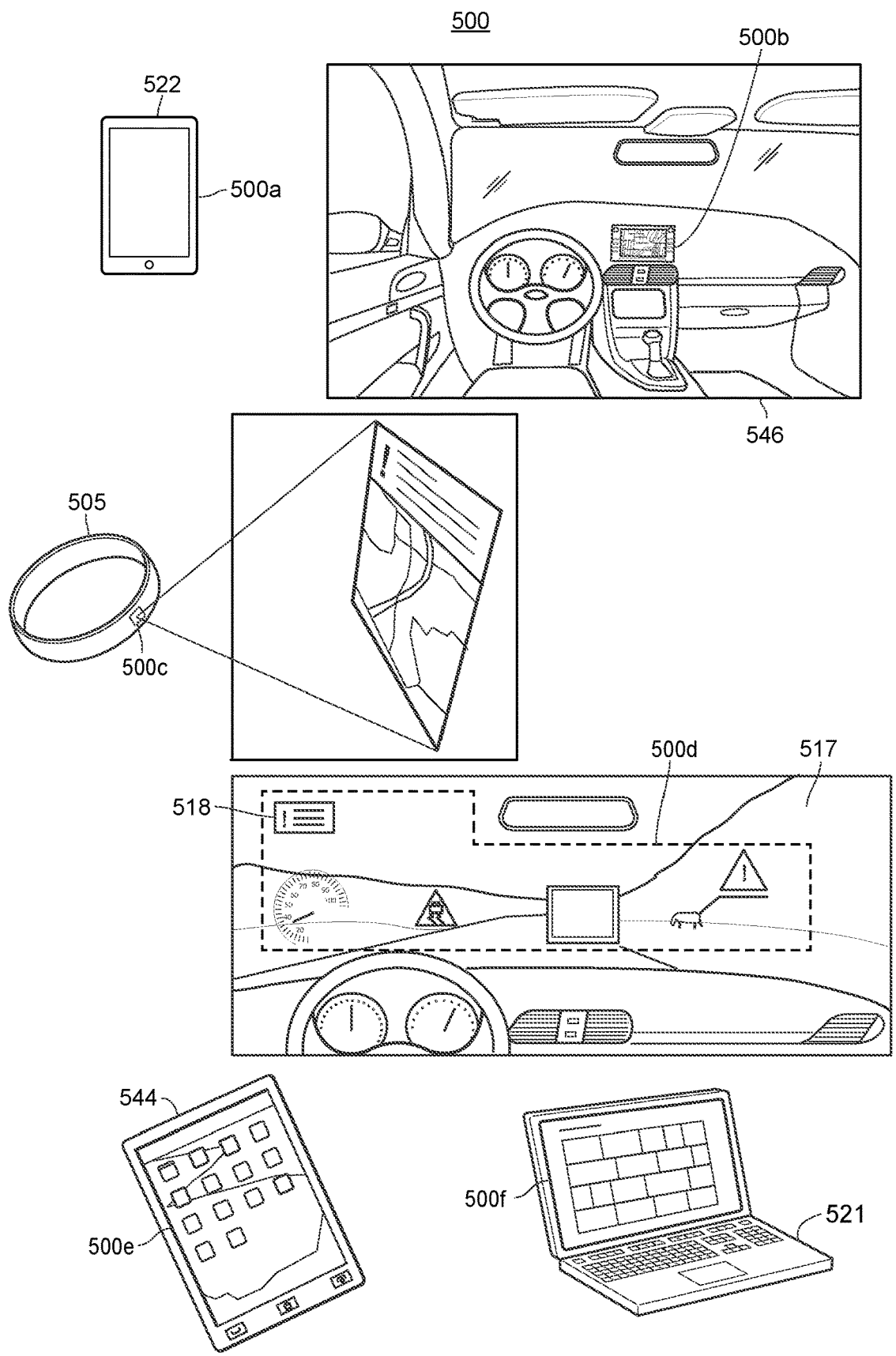
FIG. 5 illustrates example displays.

FIG. 5 illustrates a set of example display devices 500 according to various embodiments, including example displays 500a, 500b, 500c, 500d, 500e, and/or 500f that may be provided by way of a smart ring such as the smart ring 101 of FIG. 1 or 405 of FIG. 5, for the purpose of displaying information relevant to monitored impairment patterns, predicted risk exposure, and a remediating action to restore or eliminate risk exposure (e.g., providing a user notification). Each of the display devices 500 may be part of the system 100 shown in FIG. 1, and each may be utilized in place of or in addition to any one or more of the display devices shown in FIG. 1. Each display device 500 may be similar in nature to any of the display devices of ring 405, user device 422, mobile device 444, or vehicle 446 shown in FIG. 4, capable of performing similar functions and interfacing with the same or similar systems; and each of the devices 101, 405, 422, 444, and 446 may provide output via any of the displays 500a, 500b, 500c, 500d, 500e, and/or 500f, in addition to or in place of their respective displays, if desired.

In an embodiment, the display devices 500 may display the level of driving risk exposure data (e.g., as a score, a figure, a graph, a symbol, or a color field, etc.) and the suggested remediating actions (e.g., as a written text, a code, a figure, a graph, or a symbol, etc.). Examples of remediating actions will be described later in more detail. More generally, each of the display devices 500 may present visual information based at least in part upon data received from any of the devices 405, 422, 444, 446, or the server 450 shown in FIG. 4.

As shown, the display device 500a is a screen of a mobile phone 522 (e.g., representing an example of the mobile device 422) that may be coupled to the smart ring 405. The display device 500b is an in-dash display of a vehicle 546 (e.g., representing an example of a display integrated into the dash or console of the vehicle 446) that may be coupled to the smart ring 405. The display device 500c is a projector for smart ring 505 (e.g., representing an example of the smart ring 405), which could be part of the ring output unit 190 and its example output devices 390d, 390e, and 390f. The display device 500d is a heads-up display (HUD) for a vehicle (e.g., the vehicle 446) projected onto a windshield 517, which may also communicate with the smart ring 405 via the network 440. Alert 518 is a sample alert, which may display to the user any combination of a predicted level of driving risk exposer (e.g., driving risk score) and a suggested remediating action. The display device 500e is a screen for a tablet 544 (e.g., representing an example of the mobile device 444, which may communicate with the smart ring 405). The display device 500f is a screen for a laptop 521 (e.g., representing an example of the mobile device 444, which may communicate with the smart ring 405) that may be coupled to the smart ring 405.

VI. An Example Method of Developing and Utilizing a Machine Learning Model

Figure 6:
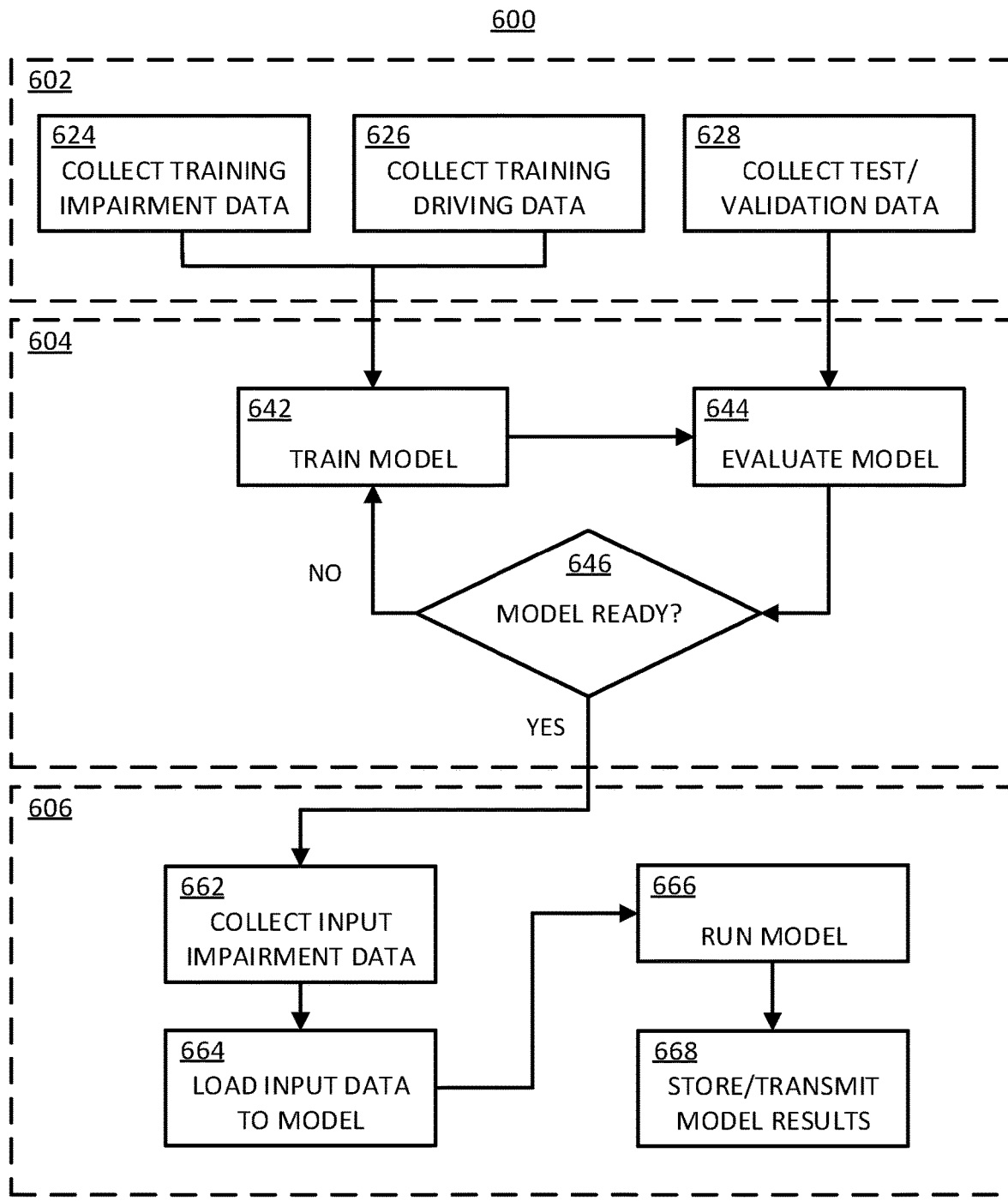
FIG. 6 shows an example method for training and utilizing a ML model that may be implemented via the example system shown in FIG. 4.

FIG. 6 depicts an example method 600 for training, evaluating and utilizing the Machine Learning (ML) model for predicting the level of driving risk exposure based at least in part upon acquired sensor data indicative of one or more impairment patterns. At a high level, the method 600 includes a step 602 for model design and preparation, a step 604 for model training and evaluation, and a step 606 for model deployment.

Depending on the implementation, the ML model may implement supervised learning, unsupervised learning, or semi-supervised learning. Supervised learning is a learning process for generalizing on problems where a prediction is needed. A "teaching process" compares predictions by the model to known answers (labeled data) and makes corrections in the model. In such an embodiment, the driving data may be labeled according to a risk level (e.g., depending on the nature and severity of swerving, braking, observed driver distraction, proximity to other vehicles, rates of acceleration, etc.). Unsupervised learning is a learning process for generalizing the underlying structure or distribution in unlabeled data. In an embodiment utilizing unsupervised learning, the system may rely on unlabeled impairment data, unlabeled driving data, or some combination thereof. During unsupervised learning, natural structures are identified and exploited for relating instances to each other. Semi-supervised learning can use a mixture of supervised and unsupervised techniques. This learning process discovers and learns the structure in the input variables, where typically some of the input data are labeled, and most is unlabeled. The training operations discussed herein may rely on any one or more of supervised, unsupervised, or semi-supervised learning with regard to the impairment data and driving data, depending on the embodiment.

A. Example of Machine Learning Model Preparation

The step 602 may include any one or more steps or sub-steps 624, 626, and 628, which may be implemented in any suitable order. At the step 624, the ML model training module 452a receives from the processor unit 454 via the communication unit 456, one or more first training data sets indicative of one or more impairment patterns for training the selected model.

In some embodiments, the one or more sets of the first training data may be collected from any suitable impairment monitoring device, for example the smart ring 405 (equipped with the one or more ring sensors 150), the user device 444 (e.g., a dedicated device for capturing impairment data), the mobile device 422 equipped with the ability to collect and transmit a variety of data indicative of impairment patterns (e.g., a smart phone), or an external database (not shown). In one embodiment, the training data may contain the user's physiological data acquired from the one or more physiological sensors, the data on the user's sweat concentration of intoxicating substances acquired from the one or more electrochemical sensors, or the user's gait data acquired from the one or more motion sensors. These data, for example, may contain measurements of the user's heart rate, blood pressure, body temperature, skin conductance, skin perfusion, sweat amount and sweat concentration of particular substances, blood levels of particular substances, body movement measurements indicating that a body is at rest or in motion and a pattern of motion, and a date and time stamp of these measurements.

In some embodiments, the first training data sets may include data indicative of impairment patterns for users other than the user associated with the smart ring, in addition to or instead of data indicative of impairment patterns for the user associated with the smart ring.

In some embodiments, the first training data set may include data indicative of the user's sleep patterns, in addition to the data indicative of impairment patterns for the same user associated with the smart ring. That is, the model may be trained on sleep data as well as impairment data. Because a lack of sleep may result in user behavior similar to that suffered due to other impairments (e.g., drug or alcohol intoxication), particular sleep patterns and particular impairment patterns may similarly be correlated to certain risky behaviors.

The first training data sets may be stored on the server memory 452, or the ring memory unit 144, or any other suitable device or its component(s).

At the step 626, the ML module 452a receives from the processor unit 454 via the communication unit 456, one or more second training data sets indicative of one or more driving patterns for training the machine learning model. This second training data may be collected from the ring 405, a vehicle computer 810 of the vehicle 446, the user device 422 (e.g., a mobile phone), the mobile device 444 (e.g., a laptop), or any other suitable electronic driving tracker configured for tracking driving patterns, or an external database (not shown) that has received the second training data from any suitable means. The data may contain tracking of the behavior of the vehicle 446, while operated by the user wearing the ring 405 (e.g., braking, accelerating/decelerating, swerving, proximity to other vehicles, adherence to lane markers and other road markers, adherence to speed limits, etc.).

In some embodiments, the second training data sets may include data indicative of driving patterns for users other than the user associated with the smart ring in addition to or instead of data indicative of driving patterns for the user associated with the smart ring.

At the step 628, the ML module receives test data for testing the model or validation data for validating the model (e.g., from one of the described respective data sources). Some or all of the training, test, or validation data sets may be labeled with a pre-determined scale of driving risk scores and thresholds indicative of trigger conditions. The developed model may utilize this scale to rank the target features of the model, and in some implementations determine the level of driving risk exposure.

B. Example of Machine Learning Model Training

The ML model development and evaluation module of the step 604, which takes place in the ML model training module 452a, may include any one or more steps or sub-steps 642 and 646, which may be implemented in any suitable order. In a typical example, at step 642, the training module 452a trains the ML model 452b by running the one or more training data sets described above. At step 644, the module 452a evaluates the model 452b, and at step 646, the module 452a determines whether or not the model 452b is ready for deployment before either proceeding to step 606 or returning to step 642 to further develop, test, or validate the model.

Regarding the sub-step 642 of the step 604, developing the model typically involves training the model using training data. At a high level, machine-learning models are often utilized to discover relationships between various observable features (e.g., between predictor features and target features) in a training dataset, which can then be applied to an input dataset to predict unknown values for one or more of these features given the known values for the remaining features. These relationships are discovered by feeding the model training data including instances each having one or more predictor feature values and one or more target feature values. The model then "learns" an algorithm capable of calculating or predicting the target feature values (e.g., high risk driving patterns) given the predictor feature values (e.g., impairment patterns).

Regarding the sub-step 644 of the step 604, evaluating the model typically involves testing the model using testing data or validating the model using validation data. Testing/validation data typically includes both predictor feature values and target feature values (e.g., including impairment patterns for which corresponding driving patterns are known), enabling comparison of target feature values predicted by the model to the actual target feature values, enabling one to evaluate the performance of the model. This testing/validation process is valuable because the model, when implemented, will generate target feature values for future input data that may not be easily checked or validated. Thus, it is advantageous to check one or more accuracy metrics of the model on data for which you already know the target answer (e.g., testing data or validation data), and use this assessment as a proxy for predictive accuracy on future data. Example accuracy metrics include key performance indicators, comparisons between historical trends and predictions of results, cross-validation with subject matter experts, comparisons between predicted results and actual results, etc.

Regarding the sub-step 646 of the step 604, the processor unit 454 may utilize any suitable set of metrics to determine whether or not to proceed to the step 606 for model deployment. Generally speaking, the decision to proceed to the step 606 or to return to the step 642 will depend on one or more accuracy metrics generated during evaluation (the step 644). After the sub-steps 642, 644, 646 of the step 604 have been completed, the processor unit 454 may implement the step 606.

C. Example of Machine Learning Model Implementation

The step 606 may include any one or more steps or sub-steps 662, 664, 666, 668, which may be implemented in any suitable order. In a typical example, the processor unit 454 collects input data (step 662), loads the input data into the model module 452b (step 664), runs the model with the input data (step 666), and stores results generated from running the model on the memory 452 (step 668).

Note, the method 600 may be implemented in any desired order and may be at least partially iterative. That is, the step 602 may be implemented after the step 604 or after the step 606 (e.g., to collect new data for training, testing, or validation), and the step 604 may be implemented after the step 606 (e.g., to further improve the model via training or other development after deployment).

Figure 7:
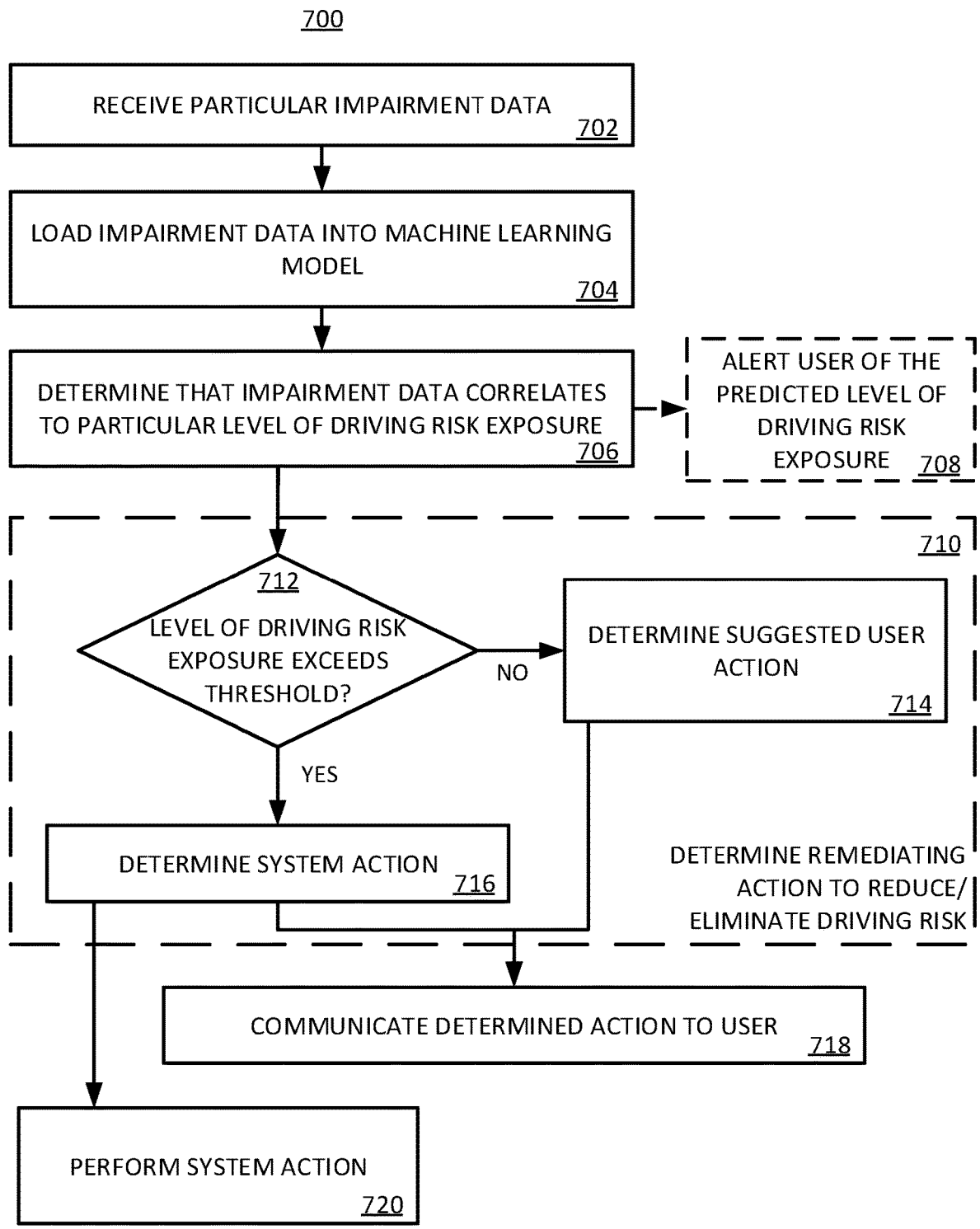
FIG. 7 illustrates example methods for assessing and communicating predicted level of driving risk exposure.

VII. Example Methods for Assessing and Communicating Predicted Level of Driving Risk Exposure FIG. 7 illustrates a flow diagram for an exemplary method 700 for implementing the ML model module 452b to: (i) predict a level of driving risk exposure to a driver (e.g., by determining the driving risk score) based at least in part upon analyzed impairment patterns; (ii) communicate the predicted risk exposure (e.g., generate a notification to alert the user of the predicted level of risk exposure); and (iii) determine remediating action to reduce or eliminate the driving risk; or communicate or implement the remediating action in accordance with various embodiments disclosed herein. Generally speaking, the described determinations regarding remediation may be made prior to the ring user attempting driving, thereby enabling the smart ring and any associated systems to prevent or discourage the user from driving while exposed to high risk due to a deteriorated cognitive or physiological state stemming from being intoxicated.

The method 700 may be implemented by way of all, or part, of the computing devices, features, and/or other functionality described regarding FIG. 1, FIG. 4, FIG. 5, and FIG. 6. At a high level, the server 450 receives impairment data and predicts a level of driving risk exposure (e.g., represented by a risk score) based at least in part upon the impairment data. In an embodiment, the predicted level of risk exposure may be a binary parameter having two possible values (e.g., high and low risk), a ternary parameter having three possible values (e.g., high, medium, low), or a parameter having any suitable number of values (e.g., a score-based parameter having a value of 0-10, 0-100, etc.). Then, based at least in part upon the predicted risk exposure, a remediation may be determined and implemented (e.g., by the system 100) or communicated to the user (e.g., via one of the example display devices 500 of the system 100, or other suitable devices of the ring output unit 190) to prevent or dissuade driving while a high exposure to risk exists.

More specifically, in an embodiment, the ML model module 452b of server 450 receives one or more particular impairment data sets from one or more data sources (step 702). In some embodiments, this data may be collected from one or more smart ring sensors 105, the user device 422 (e.g., a smart phone), or the mobile device 444 (e.g., a dedicated device for capturing impairment data). In one embodiment, the impairment data set may contain the user's physiological data acquired from the one or more physiological sensors, the data on the user's sweat concentration of intoxicating substances acquired from the one or more electrochemical sensors, or the user's gait data acquired from the one or more motion sensors. These data, for example, may contain measurements of the user's heart rate, blood pressure, body temperature, skin conductance, skin perfusion, sweat amount and sweat concentration of particular substances, body movement measurements, gait, and a date and time stamp of these measurements. In some embodiments, the data may include data indicative of the user's sleep patterns, in addition to the data indicative of impairment patterns for the same user associated with the smart ring. At step 704, the impairment data may be loaded into the ML model module 452b.

In an embodiment, at step 706 ML model module 452b may determine that particular impairment data correlates to a particular level of driving risk exposure, which is determined at step 606 of the ML model. At step 708, a communication unit of an output device of system 100 (one or more implementations of the ring output unit 190, or one or more of the display technologies depicted in FIG. 5) may alert the smart ring user of the predicted level of driving risk exposure (e.g., represented by a driving risk score). For example, the alert may be visual (e.g., a written text, an image, a color code, etc.), haptic, thermal, or an audio alert. Step 708 may or may not be implemented, depending on the embodiment. In various embodiments, an analyzing device (whether it is the server 450, or the ring 405, or the user device 422, or the mobile device 444), may use the particular impairment data and the assessed level of driving risk exposure to make a determination of a suggested action or actions to improve the particular driving risk (step 710).

In some embodiments, the analyzing device, at step 712, may assess whether the calculated driving risk exceeds a pre-determined threshold indicating that the ring user's condition is not fit for safe driving. If evaluation at step 712 yields that the driving risk score does not exceed the threshold, but presents a probability of high risk driving behavior, then further assessment at step 714 determines a suitable user action to reduce or eliminate the current driving risk. For instance, the suggested user action may be to delay driving for a certain number of hours, or abstain from consuming any additional doses, because the user has approached an allowed substance blood concentration limit dictated by a particular state for a particular class of drivers.

At step 718, similarly to step 708, a communication unit of an output device may relay to the smart ring user the suggested user action. In the case of a positive determination at step 712, the analyzing device further determines a system action (step 716), which can include one or a combination of actions to block or overtake the user's vehicle control elements 802, such as ignition 804, brakes 806, or other 808 (see FIG. 8), and at step 720 performs the system action by communicating it to vehicle controller 812.

We must note that the described paths are not mutually exclusive, and that each of the steps 718 and 720 may or may not be implemented, depending on the embodiment. For example, an implementation may select to communicate user action only, or communicate user action and system action, or communicate system action and perform system action, or perform system action only, etc.

In some embodiments, in addition to determining the level of driving risk exposure prior to a driving session based at least in part upon the driver's response to consumption of an intoxicating substance, the analyzing device may add to its analysis data indicative of the driver's impairment in real time during a driving session. As an example, the smart ring or other capable devices may collect data on the user's physiological and biochemical parameters during a driving session. The same or a different machine learning model would correlate this additional data with the saved driving data, and/or driving data of that session, and adjust the level of driving risk exposure in real time. The model may also correlate the real-time impairment data with driver compliance with the suggested remediating action. The analyzing device may then determine a new remediating user or system action. In the case of the latter, the system may interfere or overtake vehicle operation, thus preventing the user from further driving.

For instance, the smart ring system might assess the ring user's driving fitness prior to a driving session and determine a driving risk score close to a threshold score. The system may suggest to the user to rest for a certain amount of time to remediate the driving risk exposure. The driver might ignore this suggestion and initiate a driving session. After a period of time, the driver might consume more of the same or a different intoxicating substance while operating a vehicle. The ML model may process the driver's physiological and biochemical parameters, as well as real time driving data, and determine a driving risk score at or above a threshold score. In this scenario, the driver may be prevented from further driving by either stopping and parking the vehicle in a safe location or switching the vehicle into autonomous mode.

In some embodiments, any of the suggested communication systems may communicate the acquired impairment data, the determined driving risk score, the suggested remediation, and whether any actions were taken by the user, to the user's insurance provider (e.g., vehicle or health insurance provider). Such data can be used for real-time insurance adjustment, in a gamified environment of extrinsic rewards and motivators, or used in conjunction with other means of enforcing compliance with suggested remediating actions.

VIII. Example of Vehicle Control Elements and Vehicle Monitor Components

Figure 8:
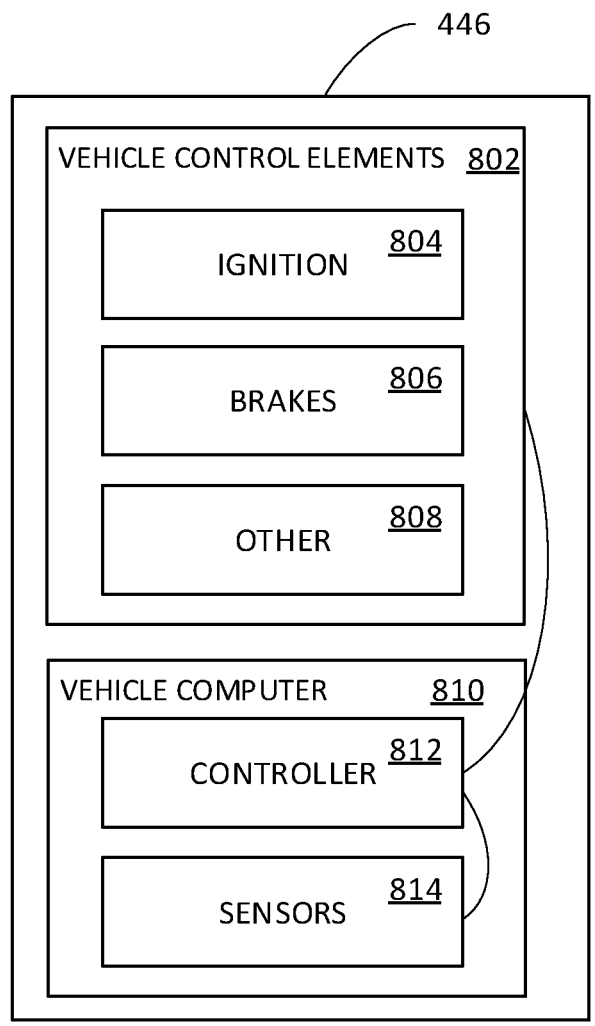
FIG. 8 shows example vehicle control elements and vehicle monitor components.

FIG. 8 shows elements of the vehicle 446 or 108, which may be in communication with the smart ring 101 or 405 and its components. Specifically, at a high level the vehicle 446 may include a set of vehicle control elements 802, which are controlled to operate the vehicle 446. The vehicle 446 may include the vehicle computer 810, which is a built-in computer system for the vehicle 446. The vehicle computer 810 may control a display (not shown) integrated into the dash or console of the vehicle 446 (e.g., to display speed, RPM, miles-per-gallon, a navigation interface, an entertainment interface, etc.) and may be referred to as a built-in vehicle computer, a carputer, an integrated vehicle computer, etc.

Vehicle control elements 802 may be in communication with other smart ring system (e.g., via vehicle controller 812), components to communicate or implement a remediating action in accordance with various embodiments disclosed therein.

The vehicle control elements may include ignition 804, brakes 806, and other components 808. As discussed below, the controller 812 may communicate with any one of the components 804-808 to prevent vehicle operation or overtake vehicle operation and resume it in autonomous mode as part of a remediation action after predicting a high driver risk exposure level or risk score. In an embodiment, vehicle sensors 814 may provide driving training data for the ML model training module 452*a*.

The vehicle computer 810 may include a controller 812 and sensors 814. While not shown, the controller 812 may include a memory and a processor, and the vehicle computer 810 may include a communication interface. The controller 812 may communicate with the vehicle control elements 802, implementing system actions of step 716. The controller 812 may also coordinate data generation and output from the sensors 814. The sensors 814 may be configured to collect data to enable tracking of the behavior of the vehicle 446 (e.g., braking, accelerating/decelerating, swerving, proximity to other vehicles, adherence to lane markers and other road markers, adherence to speed limits, etc.). The sensors 814 may include a speedometer; one or more accelerometers; one or more cameras, image sensors, laser sensors, RADAR sensors, or infrared sensors directed to the road surface, to potential obstacles on the road, or to the driver (e.g., for autonomous or semi-autonomous driving); a dedicated GPS receiver (not shown) disposed in the vehicle (e.g., in the interior, such as in the cabin, trunk, or engine compartment, or on the exterior of the vehicle); a compass; etc.

IX. Examples of Other Considerations

When implemented in software, any of the applications, services, and engines described herein may be stored in any tangible, non-transitory computer readable memory such as on a magnetic disk, a laser disk, solid state memory device, molecular memory storage device, or other storage medium, in a RAM or ROM of a computer or processor, etc. Although the example systems disclosed herein are disclosed as including, among other components, software or firmware executed on hardware, it should be noted that such systems are merely illustrative and should not be considered as limiting. For example, it is contemplated that any or all of these hardware, software, and firmware components could be embodied exclusively in hardware, exclusively in software, or in any combination of hardware and software. Accordingly, while the example systems described herein are described as being implemented in software executed on a processor of one or more computer devices, persons of ordinary skill in the art will readily appreciate that the examples provided are not the only way to implement such systems.

The described functions may be implemented, in whole or in part, by the devices, circuits, or routines of the system 100 shown in FIG. 1. Each of the described methods may be embodied by a set of circuits that are permanently or semi-permanently configured (e.g., an ASIC or FPGA) to perform logical functions of the respective method or that are at least temporarily configured (e.g., one or more processors and a set instructions or routines, representing the logical functions, saved to a memory) to perform the logical functions of the respective method.

X. Examples of General Terms and Phrases

Throughout this specification, some of the following terms and phrases are used.

Bus, according to some embodiments: Generally speaking, a bus is a communication system that transfers information between components inside a computer system, or between computer systems. A processor or a particular system (e.g., the processor 454 of the server 450) or subsystem may communicate with other components of the system or subsystem (e.g., the components 452 and 456) via one or more communication links. When communicating with components in a shared housing, for example, the processor may be communicatively connected to components by a system bus. Unless stated otherwise, as used herein the phrase "system bus" and the term "bus" refer to: a data bus (for carrying data), an address bus (for determining where the data should be sent), a control bus (for determining the operation to execute), or some combination thereof. Depending on the context, "system bus" or "bus" may refer to any of several types of bus structures including a memory bus or memory controller, a peripheral bus, or a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Communication Interface, according to some embodiments: Some of the described devices or systems include a "communication interface" (sometimes referred to as a "network interface"). A communication interface enables the system to send information to other systems and to receive information from other systems and may include circuitry for wired or wireless communication.

Each described communication interface or communications unit (e.g., communications unit 160) may enable the device of which it is a part to connect to components or to other computing systems or servers via any suitable network, such as a personal area network (PAN), a local area network (LAN), or a wide area network (WAN). In particular, the communication unit 160 may include circuitry for wirelessly connecting the smart ring 101 to the user device 104 or the network 105 in accordance with protocols and standards for NFC (operating in the 13.56 MHz band), RFID (operating in frequency bands of 125-134 kHz, 13.56 MHz, or 856 MHz to 960 MHz), Bluetooth (operating in a band of 2.4 to 2.485 GHz), Wi-Fi Direct (operating in a band of 2.4 GHz or 5 GHz), or any other suitable communications protocol or standard that enables wireless communication.

Communication Link, according to some embodiments: A "communication link" or "link" is a pathway or medium connecting two or more nodes. A link between two end-nodes may include one or more sublinks coupled together via one or more intermediary nodes. A link may be a physical link or a logical link. A physical link is the interface or medium(s) over which information is transferred and may be wired or wireless in nature. Examples of physicals links may include a cable with a conductor for transmission of electrical energy, a fiber optic connection for transmission of light, or a wireless electromagnetic signal that carries information via changes made to one or more properties of an electromagnetic wave(s).

A logical link between two or more nodes represents an abstraction of the underlying physical links or intermediary nodes connecting the two or more nodes. For example, two or more nodes may be logically coupled via a logical link. The logical link may be established via any combination of physical links and intermediary nodes (e.g., routers, switches, or other networking equipment).

A link is sometimes referred to as a "communication channel." In a wireless communication system, the term "communication channel" (or just "channel") generally refers to a particular frequency or frequency band. A carrier signal (or carrier wave) may be transmitted at the particular frequency or within the particular frequency band of the channel. In some instances, multiple signals may be transmitted over a single band/channel. For example, signals may sometimes be simultaneously transmitted over a single band/channel via different sub-bands or sub-channels. As another example, signals may sometimes be transmitted via the same band by allocating time slots over which respective transmitters and receivers use the band in question.

Machine Learning, according to some embodiments: Generally speaking, machine-learning is a method of data analysis that automates analytical model building. Specifically, machine-learning generally refers to the algorithms and models that computer systems use to effectively perform a specific task without using explicit instructions, relying on patterns and inference instead. Machine-learning algorithms learn through a process called induction or inductive learning. Induction is a reasoning process that makes generalizations (a model) from specific information (training data).

Generalization is needed because the model that is prepared by a machine-learning algorithm needs to make predictions or decisions based at least in part upon specific data instances that were not seen during training. Note, a model may suffer from over-learning or under-learning.

Over-learning occurs when a model learns the training data too closely and does not generalize. The result is poor performance on data other than the training dataset. This is also called over-fitting.

Under-learning occurs when a model has not learned enough structure from the training data because the learning process was terminated early. The result is good generalization but poor performance on all data, including the training dataset. This is also called under-fitting.

Memory and Computer-Readable Media, according to some embodiments: Generally speaking, as used herein the phrase "memory" or "memory device" refers to a system or device (e.g., the memory unit 144) including computer-readable media ("CRM"). "CRM" refers to a medium or media accessible by the relevant computing system for placing, keeping, or retrieving information (e.g., data, computer-readable instructions, program modules, applications, routines, etc.). Note, "CRM" refers to media that is non-transitory in nature, and does not refer to disembodied transitory signals, such as radio waves.

The CRM may be implemented in any technology, device, or group of devices included in the relevant computing system or in communication with the relevant computing system. The CRM may include volatile or nonvolatile media, and removable or non-removable media. The CRM may include, but is not limited to, RAM, ROM, EEPROM, flash memory, or other memory technology, CD-ROM, digital versatile disks (DVD) or other optical disk storage, magnetic cassettes, magnetic tape, magnetic disk storage or other magnetic storage devices, or any other medium which can be used to store information and which can be accessed by the computing system. The CRM may be communicatively coupled to a system bus, enabling communication between the CRM and other systems or components coupled to the system bus. In some implementations the CRM may be coupled to the system bus via a memory interface (e.g., a memory controller). A memory interface is circuitry that manages the flow of data between the CRM and the system bus.

Network, according to some embodiments: As used herein and unless otherwise specified, when used in the context of system(s) or device(s) that communicate information or data, the term "network" (e.g., the networks 105 and 440) refers to a collection of nodes (e.g., devices or systems capable of sending, receiving or forwarding information) and links which are connected to enable telecommunication between the nodes.

Each of the described networks may include dedicated routers responsible for directing traffic between nodes, and, in certain examples, dedicated devices responsible for configuring and managing the network. Some or all of the nodes may be also adapted to function as routers in order to direct traffic sent between other network devices. Network devices may be inter-connected in a wired or wireless manner, and network devices may have different routing and transfer capabilities. For example, dedicated routers may be capable of high volume transmissions while some nodes may be capable of sending and receiving relatively little traffic over the same period of time. Additionally, the connections between nodes on a network may have different throughput capabilities and different attenuation characteristics. A fiberoptic cable, for example, may be capable of providing a bandwidth several orders of magnitude higher than a wireless link because of the difference in the inherent physical limitations of the medium. If desired, each described network may include networks or sub-networks, such as a local area network (LAN) or a wide area network (WAN).

Node, according to some embodiments: Generally speaking, the term "node" refers to a connection point, redistribution point, or a communication endpoint. A node may be any device or system (e.g., a computer system) capable of sending, receiving or forwarding information. For example, end-devices or end-systems that originate or ultimately receive a message are nodes. Intermediary devices that receive and forward the message (e.g., between two end-devices) are also generally considered to be "nodes."

Processor, according to some embodiments: The various operations of example methods described herein may be performed, at least partially, by one or more processors (e.g., the one or more processors in the processor unit 142). Generally speaking, the terms "processor" and "microprocessor" are used interchangeably, each referring to a computer processor configured to fetch and execute instructions stored to memory. By executing these instructions, the processor(s) can carry out various operations or functions defined by the instructions. The processor(s) may be temporarily configured (e.g., by instructions or software) or permanently configured to perform the relevant operations or functions (e.g., a processor for an Application Specific Integrated Circuit, or ASIC), depending on the particular embodiment. A processor may be part of a chipset, which may also include, for example, a memory controller or an I/O controller. A chipset is a collection of electronic components in an integrated circuit that is typically configured to provide I/O and memory management functions as well as a plurality of general purpose or special purpose registers, timers, etc. Generally speaking, one or more of the described processors may be communicatively coupled to other components (such as memory devices and I/O devices) via a system bus.

The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

Words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

Although specific embodiments of the present disclosure have been described, it will be understood by those of skill in the art that there are other embodiments that are equivalent to the described embodiments. Accordingly, it is to be understood that the present disclosure is not to be limited by the specific illustrated embodiments.

What is claimed:

1. A method for implementing a machine learning model to predict driving risk exposure based at least in part upon observed impairment patterns, the method comprising:
receiving one or more sets of first data indicative of one or more impairment patterns collected via one or more impairment monitoring devices in a first set of smart rings, the one or more sets of first data comprising motion data collected via one or more motion sensors of the first smart ring;
receiving one or more sets of second data indicative of one or more driving patterns collected via one or more driving monitor devices, the one or more driving monitor devices including a second set of smart rings, at least a part of the one or more sets of second data being collected via one or more sensors disposed within the second set of smart rings;
utilizing the one or more sets of first data at least partially collected by the first set of smart rings and the one or more sets of second data at least partially collected by the second set of smart rings as training data for a machine learning (ML) model to train the ML model to discover one or more relationships between the one or more impairment patterns and the one or more driving patterns, wherein the one or more relationships include a relationship representing a correlation between a given impairment pattern and a high-risk driving pattern;
receiving a particular set of data collected via a particular smart ring associated with a user;
analyzing, via the ML model, the particular set of data collected by the particular smart ring associated with the user, wherein the analyzing includes:
determining that the particular set of data represents a particular impairment pattern corresponding to the given impairment pattern correlated with the high-risk driving pattern; and
in response to the determining that the particular set of data represents a particular impairment pattern, predicting, based at least in part upon the ML model, a level of risk exposure for the user during driving; and
generating a notification to alert the user of the predicted level of risk exposure.

2. The method of claim 1, wherein the one or more sets of first data comprises physiological and biochemical data collected via one or more physiological and biochemical sensors of the first set of smart rings.

3. The method of claim 1, wherein the one or more driving monitor devices includes a vehicle computer or a dedicated electronic driving tracker device;

wherein acquiring the one or more sets of second data comprises acquiring the one or more sets of second data via one or more of: the vehicle computer or the dedicated electronic driving tracker device.

4. The method of claim 1, further comprising:
providing the generated notification at one or more of: the particular smart ring, or an in-dash display of the vehicle.

5. The method of claim 1, further comprising:
comparing the predicted level of risk exposure to a known threshold to determine the predicted level of risk exposure exceeds the known threshold;
responding to determining that the predicted level of risk exposure exceeds the known threshold by generating a system action that prevents the user from operating the vehicle, wherein the preventing includes preventing the user from starting the vehicle.

6. The method of claim 1, further comprising:
comparing the predicted level of risk exposure to a known threshold to determine the predicted level of risk exposure exceeds the known threshold; and
responding to determining that the predicted level of risk exposure exceeds the known threshold by generating a system action that prevents the user from operating the vehicle, wherein the preventing includes overtaking control of the vehicle while the vehicle is in operation.

7. The method of claim 1, further comprising:
utilizing the particular set of data representing the particular impairment pattern to further train the ML model.

8. A system for acquiring data indicative of impairment patterns, and utilizing the data to predict driving risk exposure, comprising:
a server configured to:
receive the one or more sets of first data indicative of one or more impairment patterns collected via one or more impairment monitoring devices in a first set of smart rings, the one or more sets of first data comprising motion data collected via one or more motion sensors of the first smart ring;
receive the one or more sets of second data indicative of one or more driving patterns collected via one or more driving monitor devices, the one or more driving monitor devices including a second set of smart rings, at least a part of the one or more sets of second data being collected via one or more sensors disposed within the second set of smart rings;
utilize the one or more sets of first data at least partially collected by the first set of smart rings and the one or more sets of second data at least partially collected by the second set of smart rings as training data for a machine learning (ML) model to train the ML model to discover one or more relationships between the one or more impairment patterns and the one or more driving patterns, wherein the one or more relationships include a relationship representing a correlation between a given impairment pattern and a high-risk driving pattern;
receive a particular set of data collected via a particular smart ring associated with a user;
wherein the server is further configured to:
analyze, via the ML model, the particular set of data collected by the smart ring, wherein the server is configured to:
determine that the particular set of data represents a particular impairment pattern corresponding to the given impairment pattern correlated with the high-risk driving pattern; and
in response to the determining that the particular set of data represents a particular impairment pattern, predict, via the ML model, a level of risk exposure for the user during driving; and
generate a notification to alert the user of the predicted level of risk exposure.

9. The system of claim 8, wherein the one or more sets of first data comprises physiological and biochemical data collected via one or more physiological and biochemical sensors of the first set of smart rings.

10. The system of claim 8, wherein the smart ring has an inner diameter within a range between 13 mm and 23 mm.

11. The system of claim 8, wherein the server is configured to generate the notification to alert the user of the predicted level of risk exposure by way of generating the notification via the particular smart ring, a vehicle computer, or a mobile device in communication with the server.

12. The system of claim 8, wherein the one or more sets of first data includes impairment pattern data for users other than the user associated with the smart ring.

13. The system of claim 8, wherein the one or more sets of second data includes driving pattern data for users other than the user associated with the smart ring.

14. A server for implementing a machine learning model to predict driving risk exposure based at least in part upon acquired impairment patterns, the server comprising:
a communication interface;
one or more processors coupled to the communication interface; and
a memory coupled to the one or more processors and storing computer readable instructions that, when implemented, cause the one or more processors to:
receive the one or more sets of first data indicative of one or more impairment patterns collected via one or more impairment monitoring devices in a first set of smart rings, the one or more sets of first data comprising motion data collected via one or more motion sensors of the first smart ring;
receive the one or more sets of second data indicative of one or more driving patterns collected via one or more driving monitor devices, the one or more driving monitor devices including a second set of smart rings, at least a part of the one or more sets of second data being collected via one or more sensors disposed within the second set of smart rings;
utilize the one or more sets of first data at least partially collected by the first set of smart rings and the one or more sets of second data at least partially collected by the second set of smart rings as training data for a machine learning (ML) model to train the ML model to discover one or more relationships between the one or more impairment patterns and the one or more driving patterns, wherein the one or more relationships include a relationship representing a correlation between a given impairment pattern and a high-risk driving pattern;
analyze, via the ML model, a particular set of data collected by a particular smart ring associated with a user by:
determining that the particular set of data represents a particular impairment pattern corresponding to the given impairment pattern correlated with the high-risk driving pattern; and responding to said determining by predicting, based at least in part upon the ML model, a level of risk exposure for the user during driving; and generate a notification to alert the user of the predicted level of risk exposure.

15. The server of claim 14, wherein causing the one or more processors to generate the notification to alert the user of the predicted level of risk exposure comprises: causing the one or more processors to transmit the notification to any of: the smart ring, a vehicle computer, or a mobile device.

16. The server of claim 14, wherein the predicted level of risk exposure is a binary or ternary parameter.

17. The server of claim 14, wherein the one or more processors are further configured to:

compare the predicted level of risk exposure to a threshold; and when the predicted level of risk exposure exceeds the threshold, generate a system action and transmit the system action to a vehicle computer for a vehicle to cause the vehicle computer to prevent the user from operating the vehicle.

* * * * *